US012611251B2

(12) United States Patent
Chu et al.

(10) Patent No.: US 12,611,251 B2
(45) Date of Patent: Apr. 28, 2026

(54) DEVICES, ASSEMBLIES, AND METHODS FOR REMOVAL OF A BODILY MASS

(71) Applicant: Boston Scientific Scimed, Inc., Maple Grove, MN (US)

(72) Inventors: Michael S. H. Chu, Brookline, MA (US); Sacha Tang, Lowell, MA (US); Sharmad S. Joshi, Auburndale, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 246 days.

(21) Appl. No.: 17/338,307

(22) Filed: Jun. 3, 2021

(65) Prior Publication Data

US 2021/0378740 A1 Dec. 9, 2021

Related U.S. Application Data

(60) Provisional application No. 63/155,955, filed on Mar. 3, 2021, provisional application No. 63/034,065, filed on Jun. 3, 2020.

(51) Int. Cl.
| | |
|---|---|
| *A61B 18/20* | (2006.01) |
| *A61B 18/24* | (2006.01) |
| *A61B 18/26* | (2006.01) |

(52) U.S. Cl.
CPC .......... *A61B 18/201* (2013.01); *A61B 18/245* (2013.01); *A61B 18/26* (2013.01); *A61B 2218/007* (2013.01)

(58) Field of Classification Search
CPC ......... A61B 18/20; A61B 18/24; A61B 18/26; A61N 5/06
See application file for complete search history.

(56) References Cited

U.S. PATENT DOCUMENTS

| | | | | |
|---|---|---|---|---|
| 5,026,366 A | * | 6/1991 | Leckrone | A61B 18/28 606/7 |
| 5,976,130 A | * | 11/1999 | McBrayer | A61B 18/1445 606/171 |
| 6,036,685 A | | 3/2000 | Mueller | |
| 10,368,885 B2 | | 8/2019 | Wan et al. | |
| 2001/0025174 A1 | | 9/2001 | Daniel et al. | |
| 2002/0002366 A1 | | 1/2002 | Grasso et al. | |

(Continued)

FOREIGN PATENT DOCUMENTS

| | | |
|---|---|---|
| CN | 108601622 A | 9/2018 |
| DE | 202017102316 U1 | 5/2017 |
| WO | 2017136347 A1 | 8/2017 |

OTHER PUBLICATIONS

International Search Report for the International Patent Application No. PCT/US2021/035738, mailed Sep. 16, 2021, 15 pages.

*Primary Examiner* — Lynsey C Eiseman

(74) *Attorney, Agent, or Firm* — Seager Tufte Wickhem LLP

(57) ABSTRACT

The present disclosure relates generally to devices, assemblies, and methods for removing a bodily mass from a body cavity. In some embodiments, a medical device may include a scope including a working channel and a sheath having a wall defining a lumen, wherein the sheath extends beyond a distal end of the scope. The medical device may further include a laser extending through the working channel, adjacent the sheath.

6 Claims, 27 Drawing Sheets

(56)     References Cited

U.S. PATENT DOCUMENTS

| | | | |
|---|---|---|---|
| 2003/0009157 A1* | 1/2003 | Levine | ................... A61B 18/26 |
| | | | 606/7 |
| 2003/0236517 A1* | 12/2003 | Appling | ................. A61B 18/24 |
| | | | 606/7 |
| 2004/0120668 A1 | 6/2004 | Loeb | |
| 2004/0204629 A1 | 10/2004 | Knapp | |
| 2006/0036182 A1 | 2/2006 | Daniels et al. | |
| 2008/0188866 A1 | 8/2008 | Karpiel et al. | |
| 2008/0292255 A1* | 11/2008 | Stevens | ................... G02B 6/06 |
| | | | 385/117 |
| 2013/0053838 A1 | 2/2013 | Kuo | |
| 2014/0005647 A1* | 1/2014 | Shuffler | ........... A61M 25/0136 |
| | | | 29/592.1 |
| 2014/0316397 A1 | 10/2014 | Brown | |
| 2016/0235478 A1 | 8/2016 | Bonneau et al. | |
| 2017/0215899 A1* | 8/2017 | Harrah | ................... A61B 1/307 |
| 2019/0142266 A1 | 5/2019 | Casarotto | |
| 2019/0217117 A1* | 7/2019 | Barneck | ........... A61M 25/0028 |
| 2020/0093360 A1 | 3/2020 | Chu et al. | |
| 2020/0337526 A1 | 10/2020 | Chu et al. | |
| 2020/0352650 A1* | 11/2020 | Chu | ................... A61B 1/00137 |

* cited by examiner

500A 502
561
510
516
509
575
577
576
507

500B 510
561
575
502
577
516
507
509
576

500C 502
561
575
516
510
577
509
507
576

500D 510
561
575
502
577
516
507
509
576

500E 502
510
575
561
577
516
507
509
576

500F 502
577
510
561
575
516
507
509
576

500G 577
510
561
502
575
516
507
509
576

500H 502
516
507
509
510
576
575

1000

EXTENDING A SCOPE THROUGH A FIRST LUMEN OF A SHEATH, WHEREIN THE FIRST LUMEN DEFINES A SUCTION CHANNEL BETWEEN AN EXTERIOR SURFACE OF THE SCOPE AND THE SHEATH — 1010

POSITIONING THE SHEATH PROXIMATE A BODILY MASS — 1020

FRAGMENTING THE BODILY MASS USING A LASER DISPOSED WITHIN A WORKING CHANNEL OF THE SCOPE — 1030

1100

PROVIDING A SHEATH HAVING A WALL DEFINING A FIRST LUMEN ⌐1110

PROVIDING A LASER EXTENDING THROUGH THE FIRST LUMEN, WHEREIN THE FIRST LUMEN INCLUDES A SUCTION CHANNEL BETWEEN THE LASER AND THE WALL ⌐1120

POSTIONING THE SHEATH PROXIMATE A BODILY MASS ⌐1130

FRAGMENTING THE BODILY MASS USING THE LASER ⌐1140

DEVICES, ASSEMBLIES, AND METHODS FOR REMOVAL OF A BODILY MASS

PRIORITY

The present application is a non-provisional of, and claims the benefit of priority under 35 U.S.C. § 119 to, U.S. Provisional Application Ser. No. 63/034,065, filed Jun. 3, 2020, and to U.S. Provisional Application Ser. No. 63/155, 955, filed Mar. 3, 2021, the disclosures of which are herein incorporated herein by reference in their entirety.

FIELD

The present disclosure relates to medical devices and assemblies and, more particularly, to devices, assemblies, and methods for removing a bodily mass from a body cavity.

BACKGROUND

Complications resulting from the presence of bodily masses, such as hard stones, soft stones, tissue, tumors, impacted stones and the like, often require surgical intervention to remedy the problem. Lithotripsy is one type of medical procedure involving physical disruption of the bodily mass within a body cavity. During lithotripsy procedures, energy is applied to the bodily mass. Different energy sources may be used, such as electric, hydraulic, laser, mechanical, ultrasound, and the like. Laser lithotripsy, for example, uses pulsed light energy from an energy delivery device, which is converted into a mechanical and thermo energy in the form of a cavitation bubble associated with the occurrence of a shockwave. The cavitation bubble may help to disrupt, cauterize, cut and break up the bodily mass.

Many lithotripsy procedures generate particles or pollution within the body cavity as the bodily mass is disrupted and broken up. Larger stone fragments may be removed using a stone basketing technique in which one or more stone fragments are retrieved and then unloaded from the basket, external to the body, and the scope and basket are reinserted through an access sheath or ureter for the next stone fragment. However, if stone fragments are not sized correctly, visually or otherwise, before attempting basket removal, a stone fragment larger than the access sheath ID cannot be removed via the sheath. The stone fragment can also become stuck or lodged in the access sheath ID or in the basket. In more extreme cases, a blockage within the basket distal to the sheath and/or the access sheath can cause the scope itself to become stuck, thus requiring the basket handle to be disassembled and/or the entire access sheath to be removed. Additional medical intervention needed to remove the stone and/or the scope prolongs the procedure and increases risk of injury to the patient.

To help avoid the problems related to larger stones, stone fragments can be further fragmented to a fine dust size, which allows the stone dust to remain in the body for natural passage, e.g., from the kidney. In one approach, a laser fiber may be positioned alongside the retrieval basket to fragment the larger stone(s) to a smaller manageable size. However, dusting and retrieval of the stone dust is still time consuming and laborious, as the stone(s) is dusted external to the sheath and the scope is removed during suction.

The systems, devices, and methods of the current disclosure may rectify some of the deficiencies described above, and/or address other aspects of the prior art.

SUMMARY

The present disclosure in its various embodiments relates generally to medical devices, assemblies, and methods for removing a bodily mass from a body cavity. In one or more embodiments, a medical device may include a scope including a working channel, a sheath having a wall defining a lumen, wherein the sheath extends beyond a distal end of the scope, and a laser extending through the working channel, adjacent the sheath. In some embodiments, the laser may extend through the sheath. In some embodiments, the sheath may extend through the working channel. In some embodiments, the scope may extend through the sheath. In some embodiments, the lumen may be defined by an exterior surface of the scope and an interior surface of a wall of the sheath. In some embodiments, the lumen may be operable to deliver an inlet fluid flow, wherein the working channel is operable as a suction channel to draw a bodily mass towards the distal end of the scope. In some embodiments, the lumen may be defined by an interior surface of a wall of the sheath. In some embodiments, a second lumen may be defined by an exterior surface of the wall of the sheath and the working channel. In some embodiments, the laser extends through the second lumen. In some embodiments, a portion of the sheath may extend beyond the distal end of the scope to define a fragmentation chamber, wherein the laser is operable to fragment a bodily mass within the fragmentation chamber. In some embodiments, an attachment may be coupled to a distal end of the sheath, wherein the attachment includes a flared section, and wherein the attachment further defines the fragmentation chamber. In some embodiments, the attachment may include a tapered internal surface. In some embodiments, the sheath may be axially movable relative to the distal end of the scope. In some embodiments, the medical device may further include a pressure sensor located at the distal end of the scope or along the sheath. In some embodiments, the medical device may further include a deployment device coupled to a proximal end of the scope.

In one or more embodiments, a method may include providing a scope including a working channel, providing a sheath having a wall defining a lumen, the sheath extending beyond a distal end of the scope, and providing a laser extending through the working channel, adjacent the sheath. The method may further include positioning the sheath proximate a bodily mass, and fragmenting the bodily mass using the laser. In some embodiments, the method may further include applying a suction via the lumen to draw the bodily mass towards the distal end of the scope. In some embodiments, the method may further include positioning the bodily mass against a distal end of the sheath in response to the suction, and fragmenting the bodily mass while the bodily mass is positioned against the distal end of the sheath. In some embodiments, the method may further include drawing the bodily mass into a distal end of the sheath in response to the suction, and fragmenting the bodily mass while the bodily mass is positioned within the distal end of the sheath. In some embodiments, the method may further include extending the laser through the sheath. In some embodiments, the method may further include positioning the scope within the sheath.

In one or more embodiments, a suction evacuation assembly may include a scope including a working channel, a sheath having a wall defining a lumen, wherein a distal end of the sheath extends axially beyond a distal end of the scope, and a laser extending through the working channel, adjacent the sheath. In some embodiments, the laser may extend through the sheath. In some embodiments, the sheath may extend through the working channel. In some embodiments, the scope may extend through the sheath. In some embodiments, the lumen may be defined by an exterior surface of the scope and an interior surface of the wall of the sheath.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

Figure 1:
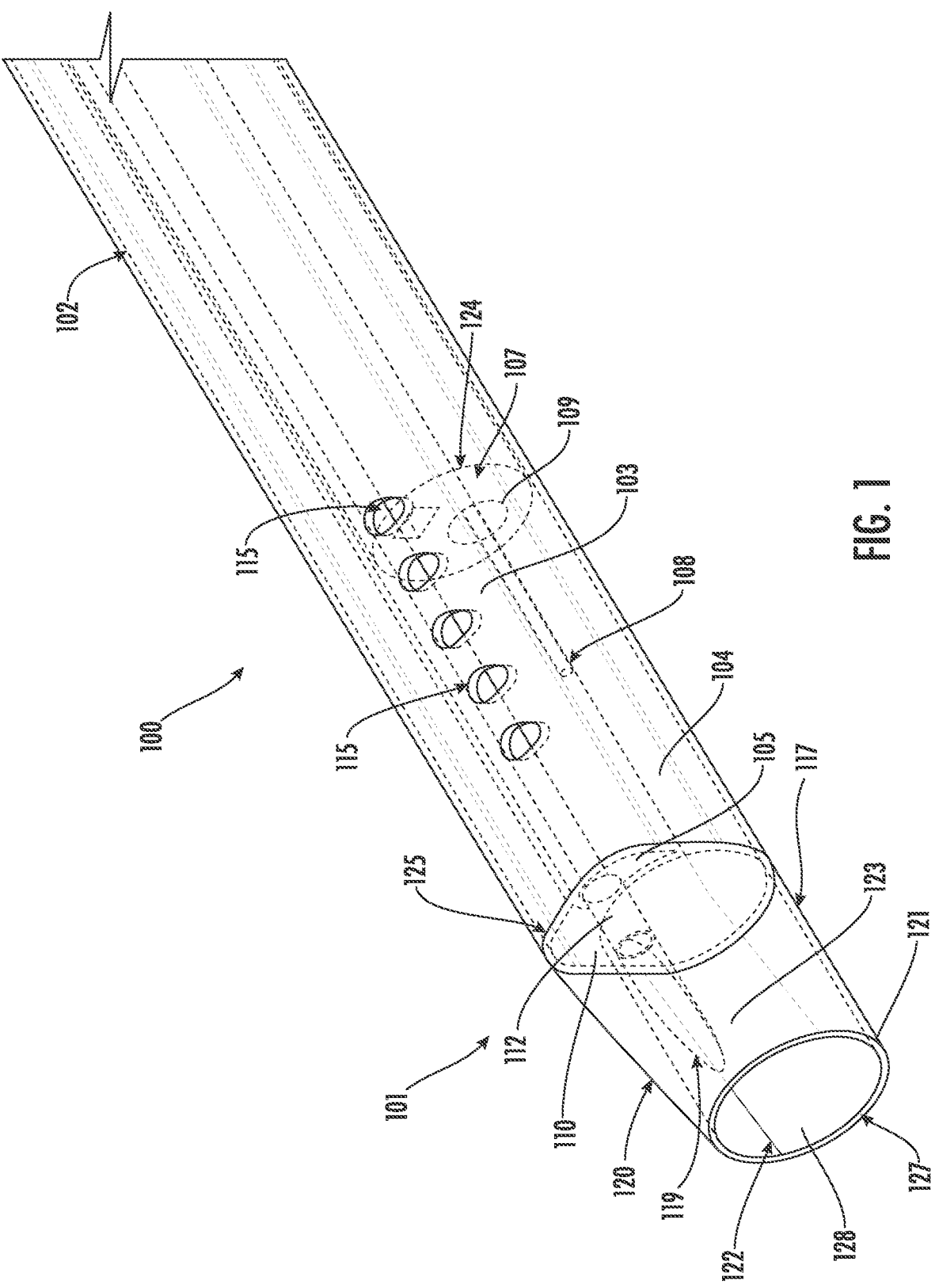
FIG. 1 is a perspective view of a distal portion of a medical device according to embodiments of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As discussed above, there is a need to have a device to fragment and extract both large stones and dust fragments from the human body using visual guidance and with minimal assistance from scopes, sheaths, laser fibers, and retrieval device exchanges, while quickening the procedure, yet still allowing for a protective sheath or access sheath like approach to stone basketing removal when required or preferred. As such, embodiments herein may provide a sheath used in conjunction with an endoscope (hereinafter "scope"), such as a flexible ureteroscope. In some approaches, a disposable scope may be used, as stone dust can cause scrapes, blockages, or other damage to the scope.

Examples described herein include systems, devices, and methods to facilitate and improve the efficacy, efficiency, and safety of medical procedures to break up and remove bodily masses, such as hard stones, soft stones, tissue, tumors, impacted stones, and the like. For example, aspects of the present disclosure may provide an operator (e.g., a physician, medical technician, or other medical service provider) with the ability to more easily apply laser energy from an energy source to a kidney stone and apply suction or a vacuum force to secure the stone to be lasered (e.g. at the tip of the sheath or within the sheath) and remove the resultant stone dust. Furthermore, aspects of the present disclosure may allow an operator to deliver energy, deliver irrigation, and apply suction within a body cavity, and breakup a clog or blockage within the suction tube without the need to remove medical devices from the body cavity. Some aspects of the present disclosure may be used in performing an endoscopic, hysteroscopic, or ureteroscopic procedure.

In some approaches, larger stones can be lasered to size, with or without visualization, to fit into a distal inside diameter (ID) of the sheath via suction. The stone/fragment suctioned by the sheath may be held at the distal tip of the sheath or in a lumen of the sheath while the laser fragments the stone to a smaller size and/or to dust. In some approaches, a stone fragmenting technique may be used, such as directly aiming the laser at the stone. In another stone fragmenting technique, the laser is energized randomly at repulsing/passing stones, fragmenting the stone within a confined space. In some embodiments, stone dust from the fragmented stone is suctioned through a working channel of the scope, alongside the laser fiber, or in the entire working channel of the scope when the laser fiber is removed.

In some approaches, a dedicated stone dust suction passageway or suction channel may be provided alongside the scope for stone dust removal while the scope shaft remains within the sheath, e.g., at a distal portion. Thus, visualization may be provided as the stone dust is removed in a fluid medium via suction, aspiration, or pulsation. In some embodiments, the suction channel may include an internal taper or a step taper, which is used with the outer distal diameter of the endoscope to gauge the dust size, allowing only dust smaller than the passageway to enter.

In yet other embodiments including a suction channel, a distal tip of the scope may be moved to the taper portion to allow stone dust to be evacuated out of the suction channel. Alternatively, the scope may be vacated (e.g., drawn proximally), entirely or partially, from the lumen and into a fitting chamber to increase or to expand the lumen of the suction channel to include the space that was occupied by the scope shaft. This may be beneficial to permit passage of larger stones.

In yet other embodiments, clogged dust in or between the suction channel and the scope can be cleared by moving the scope shaft proximal to the clog. Alternatively, the laser can be energized to fragment dust clogs in the lumen of the sheath, distal to the scope tip under visualization. In some embodiments, the fragments are further yet fragmented to a smaller size, e.g., micro dust or smaller, such that dust clogs do not form. Means for unclogging the sheath may also be provided. In another embodiment, an additional lumen may be used for infusion of a fluid medium through a distal or side port to aid with suction and removal of the dust. In certain embodiments, the sheath replaces the need for a retrieval basket. Using the sheath beneficially eliminates the need or concerns for sizing the stone for sheath ID fit, as the stone can be fragment further in the lumen of the sheath.

In certain embodiments, the sheath need not be removed and exchanged during a procedure for another medical device, as the laser, scope, and sheath operate to hold, reposition, and fragment stones distal to the sheath, as well as downsize stones internal to the sheath. The sheath is also capable of removing stones. In certain embodiments, the working channel of the scope provides fluid communication with the lumen of the sheath.

Figure 2:
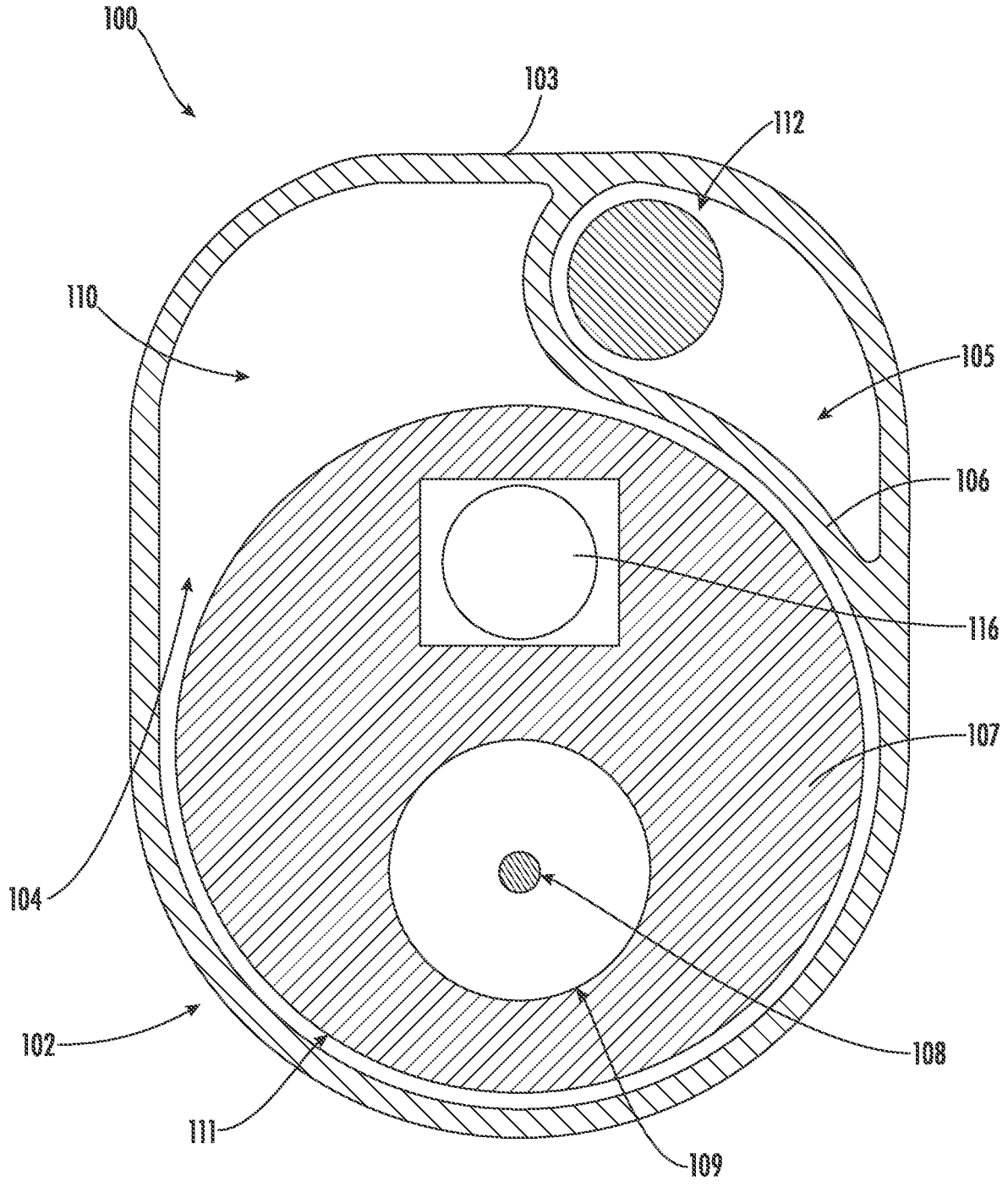
FIG. 2 is an end cross-sectional view of the medical device of FIG. 1 according to embodiments of the present disclosure.
Figure 3:
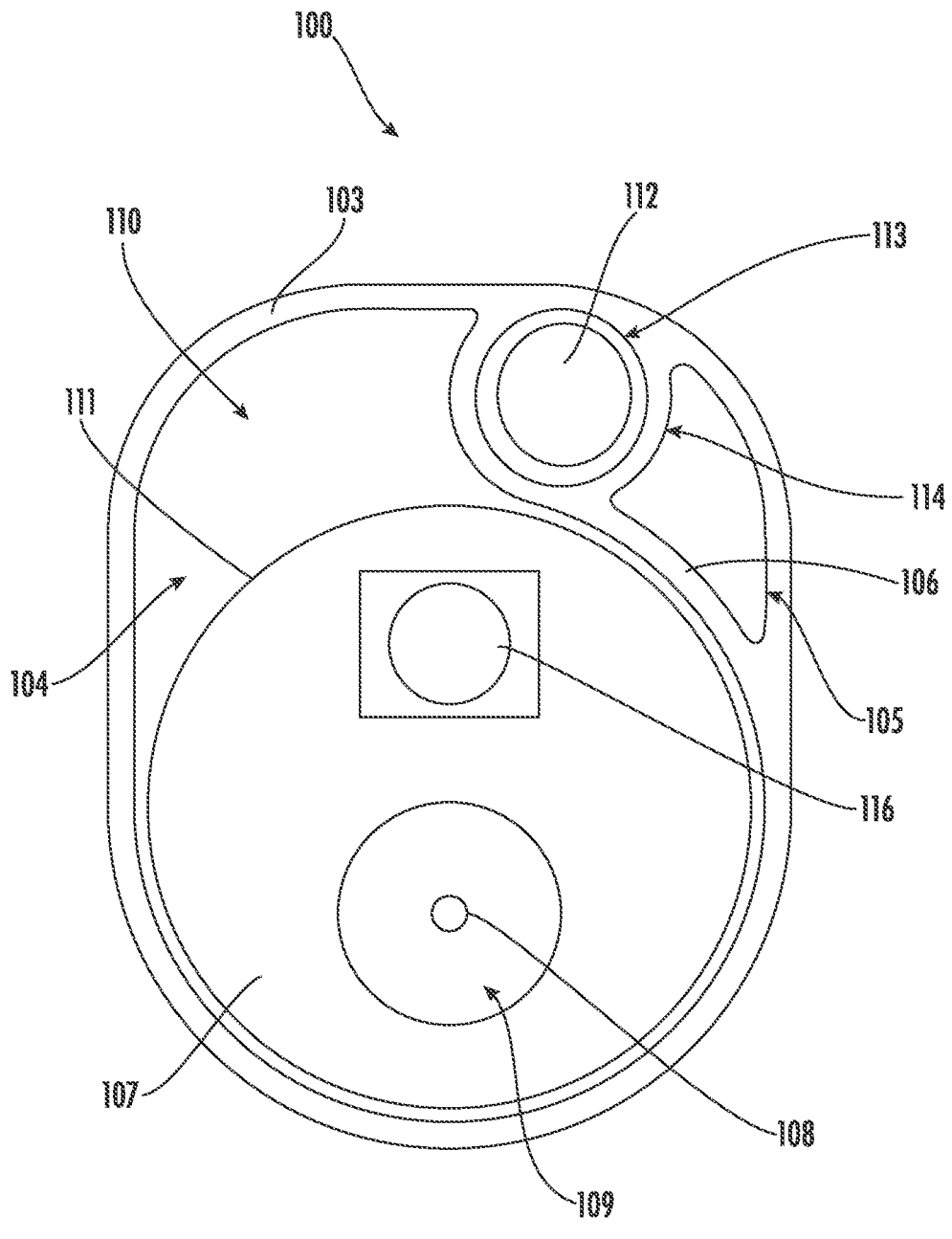
FIG. 3 is an end cross-sectional view of the medical device of FIG. 1 according to embodiments of the present disclosure.

Turning now to FIGS. 1-3, a portion of a medical device (hereinafter "device") 100, such as a suction evacuation assembly or system, will be described. As shown, a distal end 101 of the device 100 may include a sheath 102 having a wall 103 defining a first lumen 104 and a second lumen 105. In some embodiments, the wall 103 may include a first wall section 106 extending across a central area of the sheath 102 to define the first and second lumens 104, 105. A scope 107 may extend through the first lumen 104, the scope 107 including a laser 108 (e.g., a laser fiber) extending through a working channel 109 thereof. As will be described in greater detail herein, the laser 108 can be exposed or extended from a distal end 124 of the scope 107 and/or sheath 102 to fragment/dust a bodily mass, such as one or more renal stones, upon impact. In various embodiments, the laser 108 can be positioned relative to the sheath 102 and the scope 107 by advancing or retracting the laser 108 from the scope 107 manually or by using a powered mechanical deployment device. The scope 107 may include a feedback or visualization device 116 (FIGS. 2-3) at a distal end thereof.

As better viewed in FIGS. 2-3, the first lumen 104 defines a suction channel 110 between an exterior surface 111 of the scope 107, the wall 103, and the first wall section 106. The shape or profile of the wall 103 and the first wall section 106 helps to maintain the scope 107 in a desired position. For example, the scope 107 may generally be positioned off-center within the first lumen 104 to permit a larger area for the suction channel 110. In some embodiments, the device 100 may include a sensor 112 (e.g., pressure sensor or a guide wire sensor) to control inlet and outlet flow via an automated fluid management system (FMS), e.g., to avoid over and under pressurizing the kidney. In the non-limiting embodiment shown in FIG. 2, the sensor 112 extends through the second lumen 105. In the non-limiting embodiment of FIG. 3, the sensor 112 may extend through a third lumen 113, which is defined in part by a second wall section 114 and the first wall section 106.

Referring again to FIG. 1, in some embodiments, the device 100 may include an angled tip 117 at a distal end 125 of the sheath 102. During use, the angled tip 117 beneficially eases an otherwise blunt tip of the sheath 102 for introduction through, e.g., the ureteral orifice. As shown, the sensor 112 may extend through a tip opening 119 in an outer surface 120 of the angled tip 117. The angled tip 117 may include an external tip wall 121 and an internal tip wall 128 together defining a tip lumen 122 for receiving stones or stone dust (not shown) therein. Between the external tip wall 121 and the internal tip wall 128 is a tip chamber 123. In the non-limiting embodiment shown, the suction channel 110 may be closed off from the tip chamber 123 at the distal end 125 of the sheath 102. In other embodiments, the suction channel 110 is fluidly connected with the tip chamber 123 within the angled tip 117 to blend into the tip lumen 122. In this example, the tip lumen 122 may be just slightly larger than an outside diameter (OD) of the scope 107.

As further shown, the device 100 may include one or more fluid openings 115 extending through the wall 103 of the sheath 102. In various embodiments, the fluid openings 115 may extend from the second lumen 105 and/or the third lumen 113. During use, the fluid openings 115, the suction channel 110, and the second lumen 105 and/or the third lumen 113 are in fluid communication. In some embodiments, the fluid openings 115 may further be in fluid communication with the tip chamber 123. For example, fluid may travel distally within the second lumen 105, exiting the fluid openings 115 and traveling into the body cavity. From the body cavity, the fluid is then drawn into the tip chamber 123 and then through the suction channel 110. The flow of the fluid through the device 100 creates the suction force to draw the stones and/or stone dust towards the scope 107 to hold, reposition, and fragment (e.g., by the laser 108) stones distal to a tip distal end 127, as well as downsize stones internal to the first lumen 104 and/or the tip lumen 122. Although a total of five (5) fluid openings 115 are shown, it'll be appreciated that a greater or lesser number of fluid openings may be possible in alternative embodiments.

In some embodiments, once the sheath 102 is brought into a desired position within the body cavity, a stone (not shown) may be suctioned to the tip distal end 127 of the angled tip 117, either for transport to another location or to be downsized by the laser 108, e.g., to a micro dust size. In some embodiments, the size/volume of the stone can be viewed via the visualization device 116 to determine, e.g., optimal volume removal and stone size passability. Once the stone is downsized, or if the stone is already small enough, the stone can be brought into the tip lumen 122 and "popcorned," i.e., impacted by the laser 108 to cause the stone and the resulting fragments to bounce around the tip lumen 122 and/or the first lumen 104 of the sheath 102. It will be appreciated that the position of the scope 107 may influence where along the sheath 102 the stone fragments are popcorned. For example, the scope 107 may extend to the distal end 125 of the sheath 102, thus causing the stone fragments to be confined within the tip lumen 122. In other embodiments, the scope 107 can be withdrawn proximally within the sheath 102, which in turn allows the stone fragments to be drawn into the first lumen 104, e.g., proximal the distal end 125 of the sheath 102. This withdrawn scope position provides a deeper and larger volume for the stone fragments, which helps prevent the stone fragments from being expelled by the laser 108 out of the angled tip 117. In some embodiments, the stone fragments can be collected as soon as the distal end 124 of the scope 107 clears the distal end 125 of the sheath 102, e.g., without having to remove the entire shaft of the scope 107 from the body first lumen 104 for ease of reinsertion of the scope 107 back into position.

In some embodiments, the sheath 102 can be introduced into the human body over a dilator (not shown) or introduced backloaded over a flexible ureteroscope and guided over a guidewire, e.g., into the ureter or ureteropelvic junction (UPJ). The scope 107 can then be inserted into the sheath 102, and advanced into the kidney, for example. The distal flexible tip of the sheath 102 may then be advanced over the scope 107 when needed. When the sheath 102 is introduced over the shaft of the scope 107, it can be abutted such that a user can grip and guide the distal uncovered/unsheathed scope 107 with his/her guide hand. In some embodiments, the sheath 102 and the scope 107 are sealed by, e.g., an 0-ring therebetween. The device 100 may be for single-use and therefore disposable, or may be reusable.

Furthermore, in some embodiments, the sheath 102 can be manually operated via a control aperture by a user with an electric pump (not shown), or automated with an FMS and data of a pressure sensor, such as the sensor 112. It will be appreciated that multiple sensors 112 may be present within the sheath 102 to measure other parameters. The collected sensor data can be used to control the flow via the FMS.

Figures 4A, 4B:
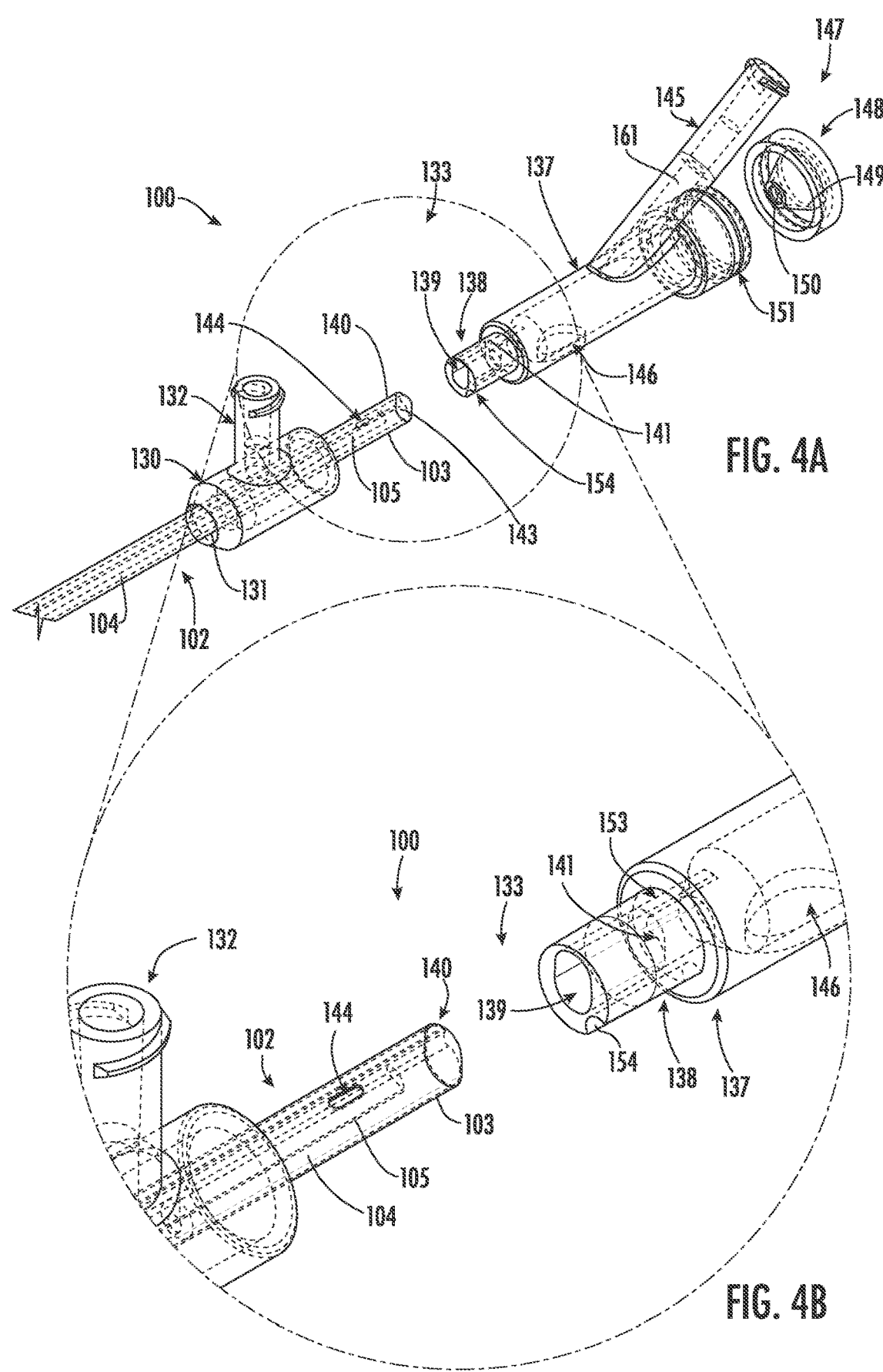
FIG. 4A is a perspective view of a proximal portion of the medical device of FIG. 1 according to embodiments of the present disclosure.
FIG. 4B is a close-up perspective view of the proximal portion of the medical device of FIG. 4A according to embodiments of the present disclosure.

FIGS. 4A-4B demonstrate a proximal portion 133 of the device 100 according to embodiments of the present disclosure. As shown, the device 100 may include an inlet body 130 coupled with the sheath 102, the inlet body 130 being in fluid communication with the second lumen 105 and/or the third lumen 113 (not shown) via a skive hole 144 at a proximal end 140 of the sheath 102. In some embodiments, the skive hole 144 may be used for fluid inlet and/or a sensor lead wire exit. The proximal end 140 of the sheath 102 may further include a sealed end 143 (e.g., glue), which seals the second lumen 105 and/or the third lumen 113. It will be appreciated that a glue, epoxy or the like can be used to seal and bond various joints, shaft, and bodies together such that inlet body 130 and the outlet body 137 are not in fluid communication. The sheath 102 may extend through a central opening 131 of the inlet body 130, the inlet body 130 further including an inlet port 132 extending therefrom. Although non-limiting, the inlet port 132 may generally extend perpendicular to the inlet body 130, as shown, or at an angle.

The device 100 may further include an outlet body 137 coupleable with the inlet body 130, the outlet body 137 in fluid communication with the first lumen 104. In some embodiments, the outlet body 137 may include a fitting 138 at a distal end thereof, the fitting 138 including a channel 139 for receiving the proximal end 140 of the sheath 102. As shown, a shape/profile of the channel 139 generally compliments the shape/profile of the wall 103 of the sheath 102. In some embodiments, the fitting 138 may include an internal stop surface 141, which prevents the sheath 102 from entering further into the outlet body 137. The fitting 138 may further include a channel or groove 153 for a sensor lead (not shown). The sensor lead connects with a distal end of the sensor and may have a connector at a proximal end, such as a USB connector, or the like.

The outlet body 137 may further include a suction port 145 and a control aperture 146 to aid with suction control. A lumen 161 of the suction port 145 may be sealed or otherwise air-tight such that a suction force within the device 100 is not lost as the suction travels from the proximal end to the distal end. In some embodiments, the control aperture 146 offers a manual pressure/suction control and can alternatively be used with an electric pump. For example, an operator may cover the control aperture 146 with his/her thumb to prevent suction from being lost. It will be appreciated that partially covering the control aperture 146 can control the magnitude of the suction. In some embodiments, the control aperture 146 may not be needed if the FMS is used, for example.

As further shown in FIG. 4A, a proximal end 147 of the outlet body 137 may include an elastomeric cap 148 including a funnel 149 and a central hole 150 that may be smaller than the OD of the scope (not shown) to seal against the exterior surface of the scope to prevent suction force from being lost. The elastomeric cap 148 may couple to a cap engagement surface 151 of the outlet body 137.

Figures 5A, 5B:
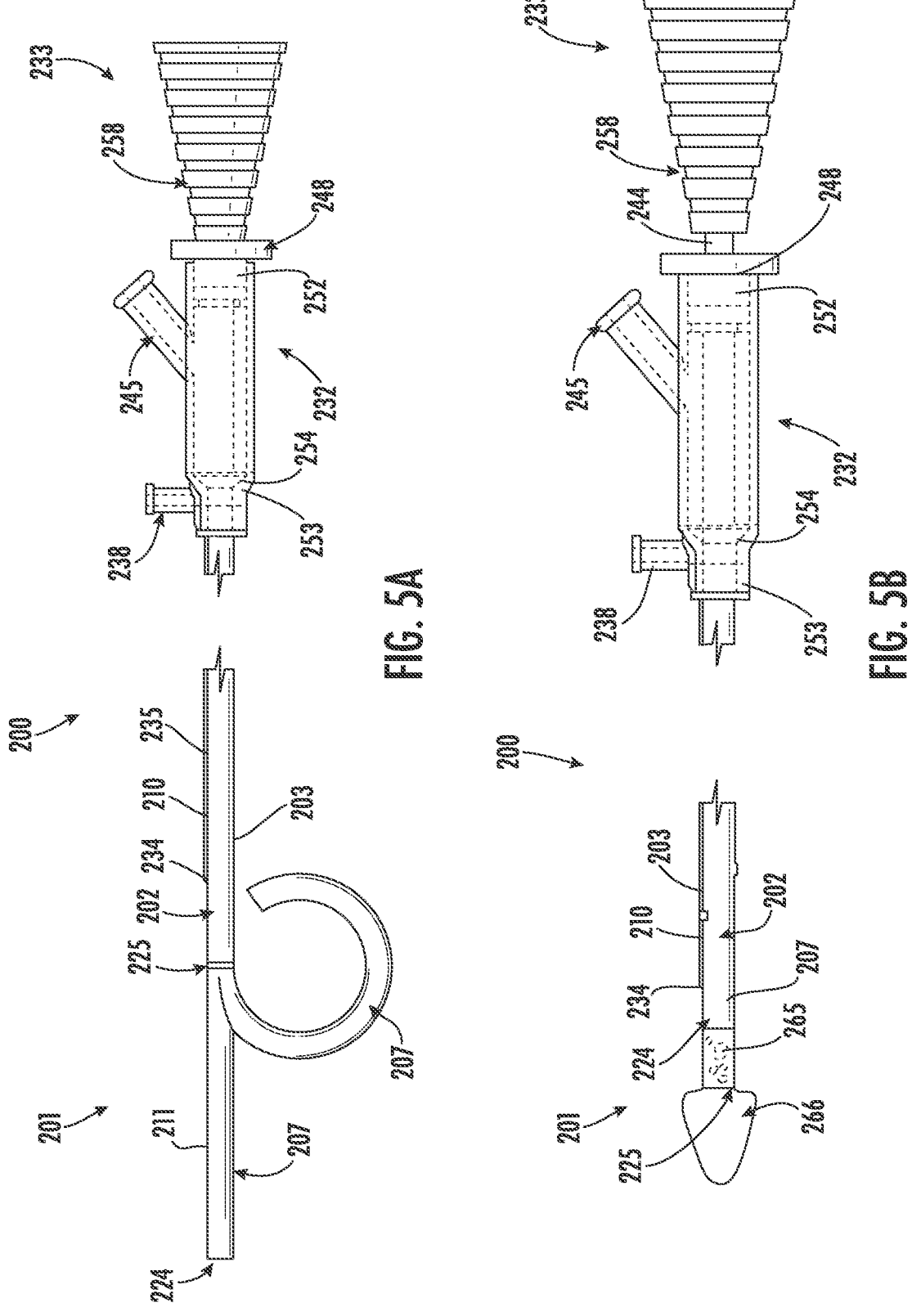
FIGS. 5A-5C depict various side views of a medical device according to embodiments of the present disclosure.
Figure 5C:
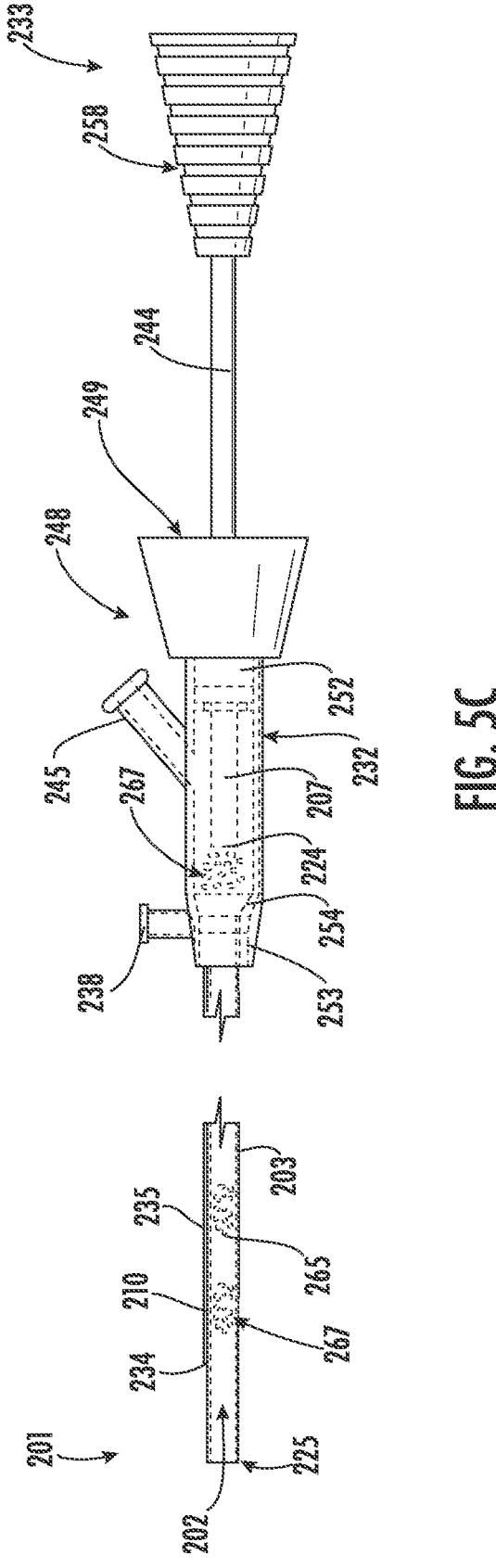

Turning now to FIGS. 5A-5C, a device 200, such as a suction evacuation assembly, will be described. As shown, a distal end 201 of the device 200 may include a sheath 202 and a scope 207 within a lumen defined by a wall 203 of the sheath 202, while a proximal end 233 of the device 200 may include a body 232, which is in fluid communication with the lumen of the sheath 202. In some embodiments, the scope 207 may include a laser (not shown) extending through a working channel thereof. As shown, the sheath 202 may further include a suction channel 210, which may be external to the first lumen of the sheath 202. The suction channel 210 may include a first end 234 in fluid communication with an inlet port 238. Although non-limiting, a wall 235 defining the suction channel 210 may have a flattened profile.

The body 232 may include a suction port 245, a rigid threaded cap 248 containing a through aperture, and an elastic grommet 252. Proximal of the rigid threaded cap 248 may be a strain relief 258 of a scope handle (not shown). In some embodiments, the body 232 may further include a fitting 253 at a distal end thereof, the fitting 253 having a tapered section 254. The fitting 253 may couple the sheath 202 to the body 232.

Although not limited to any specific size or shape, the sheath 202 OD or profile is preferably kept at a minimum to avoid possible over dilatation injuries to the ureters. A distal end 225 of the sheath 202 may be circular, having an ID that is only slightly larger than the OD of the scope 207. A space between an outer surface 211 of the scope 207 and an inner surface of the sheath 202 allows for fluid and suction communication. In some embodiments, the distal end 225 of the sheath 202 is made of a flexible polymer, which is stiff enough to be pushed distally and pulled proximally to follow and slide over the curvature of a deflected distal end 224 of the scope 207, e.g., into the lower pole of the kidney. In other embodiments, the distal end 225 of the sheath 202 is positioned over the distal end 224 of the flexible scope 207 before the scope 207 is deflected. Although not shown, the sheath 202 can be reinforced with a coil or a braid made of polymer or metal. In some embodiments, the distal end 225 of the sheath 202 may be internally lined with a polytetrafluoroethylene (PTFE) or expanded PTFE, which is a highly lubricious, flexible, and laser resistant material. EPTFE may be porous, allowing it to absorb water, which is beneficial as laser energy dissipates through water. When the sheath 202 is transparent, the water within the sheath 202 may prevent the laser from escaping radially in an unintended direction. In various embodiments, EPTFE or PTFE can extend partially or entirely along the length of the sheath 202.

In some embodiments, the distal end 225 of the sheath 202 can be extended or retracted relative to the distal end 224 of the scope 207. When extended, the sheath 202 forms or provides a distal, open-ended enclosure 265, as shown in FIG. 5B. The enclosure 265 can be distally closed off against, e.g., a stone 266, or against a wall of the kidney. The distal end 224 of the scope 207, when situated proximal to the distal end 225 of the sheath 202, provides a proximal stop for fragments of the stone 266. It will be appreciated that a position of the distal end 224 of the scope 207 relative to the distal end 225 of the sheath 202 may change the volume of the enclosure 265. In some embodiments, the scope 207 may further include a camera and/or lights for visualization and a working channel for fluid communication. The working channel may also provide access for one or more elongate devices, such as a laser fiber and/or retrieval devices.

During use, the stone 266 may be suctioned to the distal end 225 of the sheath 202, as shown in FIG. 5B, either for transport to another location or to be downsized by the laser, e.g., to a micro dust size. The enclosure 265 can contain dust or fragments 267 from the stone 266 for convenient containment, gathering, and storage for later removal. Fragments 267 can be popcorned within the interior of the enclosure 265 for a desired duration to achieve a smaller dust size. In some embodiments, the size/volume of the fragments 267 can be viewed via the scope camera to determine, e.g., optimal volume removal and stone/fragment size passability. The scope 207 can also be withdrawn further proximal within the sheath 202, as shown in FIG. 5C, to provide enclosure 265 with a deeper and larger volume, which helps prevent laser repulsed fragments 267 from escaping out of the distal end 225 of the sheath 202. In some embodiments, a shaft 244 of the scope 207 may be drawn proximal a funnel 249 until the distal end 224 of the scope 207 is disposed within an interior of the body 232.

Applying a suction force in the proximal direction of the enclosure 265 aids to retain the fragments 267. The enclosure 265 may transport the fragments 267 out of the body 232 through a working channel of the scope 207 and/or the lumen of the sheath 202. In some embodiments, removal of the fragments 267 can also occur by applying suction to the suction port 245 as the shaft 244 is being drawn proximally, with or without visualization. As shown, the fragments 267 may be drawn into the interior of the body 232. Although not shown, in some embodiments, a Tuohy Borst adapter or seal, such as a duck bill valve, can self-close to seal off the lumen of the scope 207. Thus, suction may be applied to the distal end 225 of the sheath 202 without escaping from the proximally located suction port 245.

Furthermore, suction can be applied, or intermittently applied, through the sheath 202 via the suction port 245, which may be angled rather than oriented at approximately 90°, similar to the inlet port 238. As shown, the inlet port 238 may be located proximal of, and is in fluid communication with, the interior of the body 232. In some embodiments, the inlet port 238 can also be angled. Other types of connectors are acceptable in different embodiments. Fluids can be injected or infused through the suction channel 210 and lumen of the sheath 202, if warranted.

In some embodiments, the fragments 267 can be collected as soon as the distal end 224 of the scope 207 clears the distal end 225 of the sheath 202, e.g., without having to remove the entire shaft 244 of the scope 207 from the body 232, for ease of reinsertion of the scope 207 back into the sheath 202 for the next stone. In some embodiments, as shown in FIG. 5C, the rigid threaded cap 248 may include the funnel 249 for ease of insertion or reinsertion of the scope 207 when the shaft 244 is totally removed from the sheath 202 and/or the body 232. The distal end 224 of the shaft 244 of the scope 207 can also rest in the funnel 249 for easier reinsertion in some embodiments.

Furthermore, in some embodiments, the sheath 202 can be manually operated via a control aperture (not shown) of the body 232, e.g., using an electric pump, or automated with FMS and data of a pressure sensor. Additionally, the sheath 202 can be managed by an FMS, which can be used to direct/monitor inlet and outlet flow. A sensor (not shown), such as a pressure sensor, can be placed in the sheath 202 at the distal end 225, along with other sensors to measure other parameters. The collected data can be used to control the flow via FMS.

In another embodiment, the sheath 202 ID is larger than the scope 207 OD to allow dust passage therebetween. In some embodiments, the shaft 244 of the scope 207 is coaxial to the sheath 202, and a taper of the wall 235 of the suction channel 210 connects lumens therebetween. In other embodiments, the scope 207 and the suction channel 210 may share the same lumen coaxially, as will be described in greater detail herein. In yet another embodiment, the inlet port 238 and the suction channel 210 are separate from the sheath 202 to allow for continuous inlet fluid communication with the distal end 225 of the sheath 202 to, e.g., replenish fluid that has been suctioned out with the fragments 267. Alternatively, fluid can be aspirated in and out the same lumen of the sheath 202. In another embodiment, the suction channel 210 may be an integral part of the sheath 202, extending through the sheath 202 to the distal end 225 thereof. As shown, the first end 234 of the suction channel may be located proximal to the distal end 225 of the sheath 202.

Figures 6A, 6B:
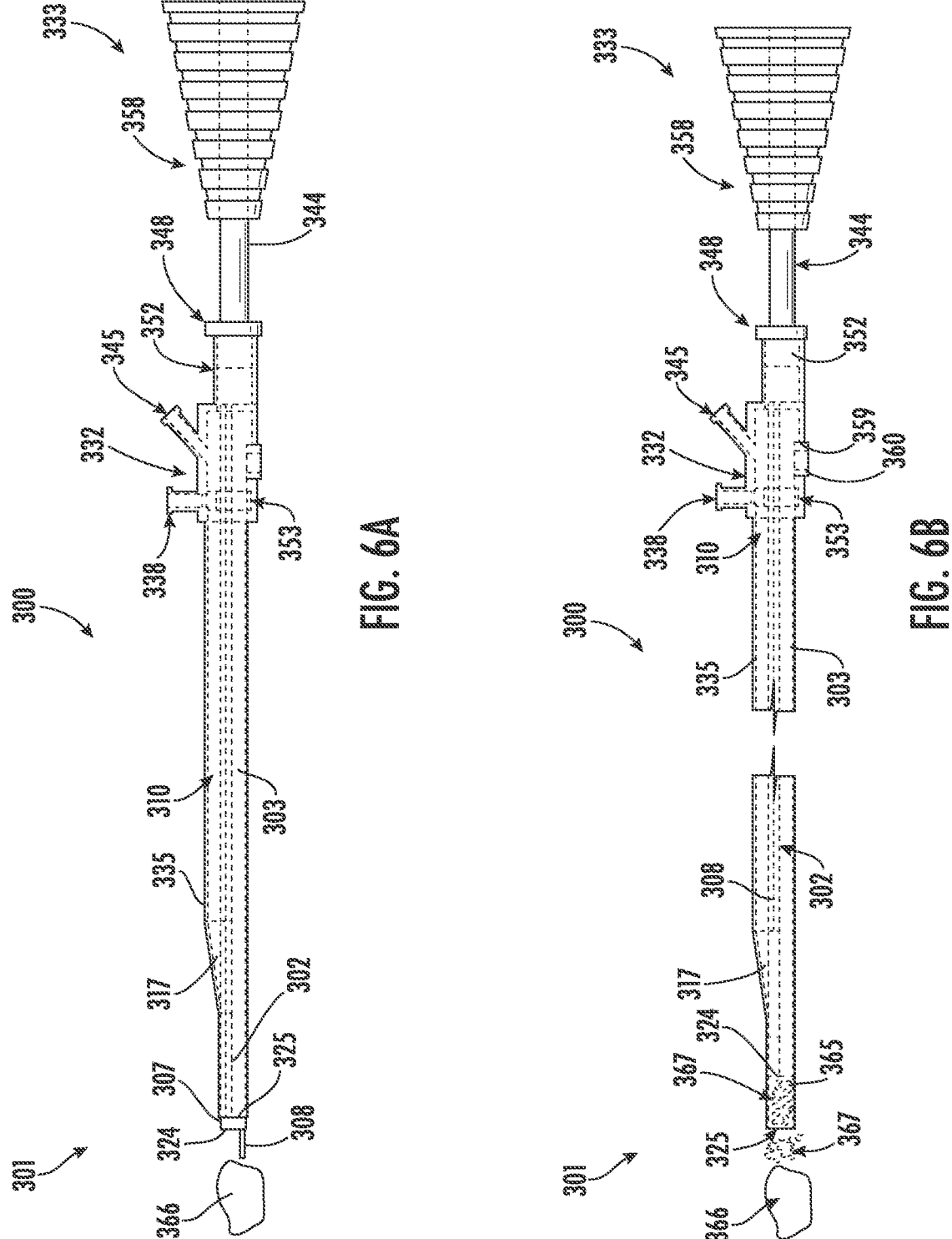
FIGS. 6A-6C depict side views of a medical device according to embodiments of the present disclosure.
Figures 6C, 7A, 7B, 7C, 7D:
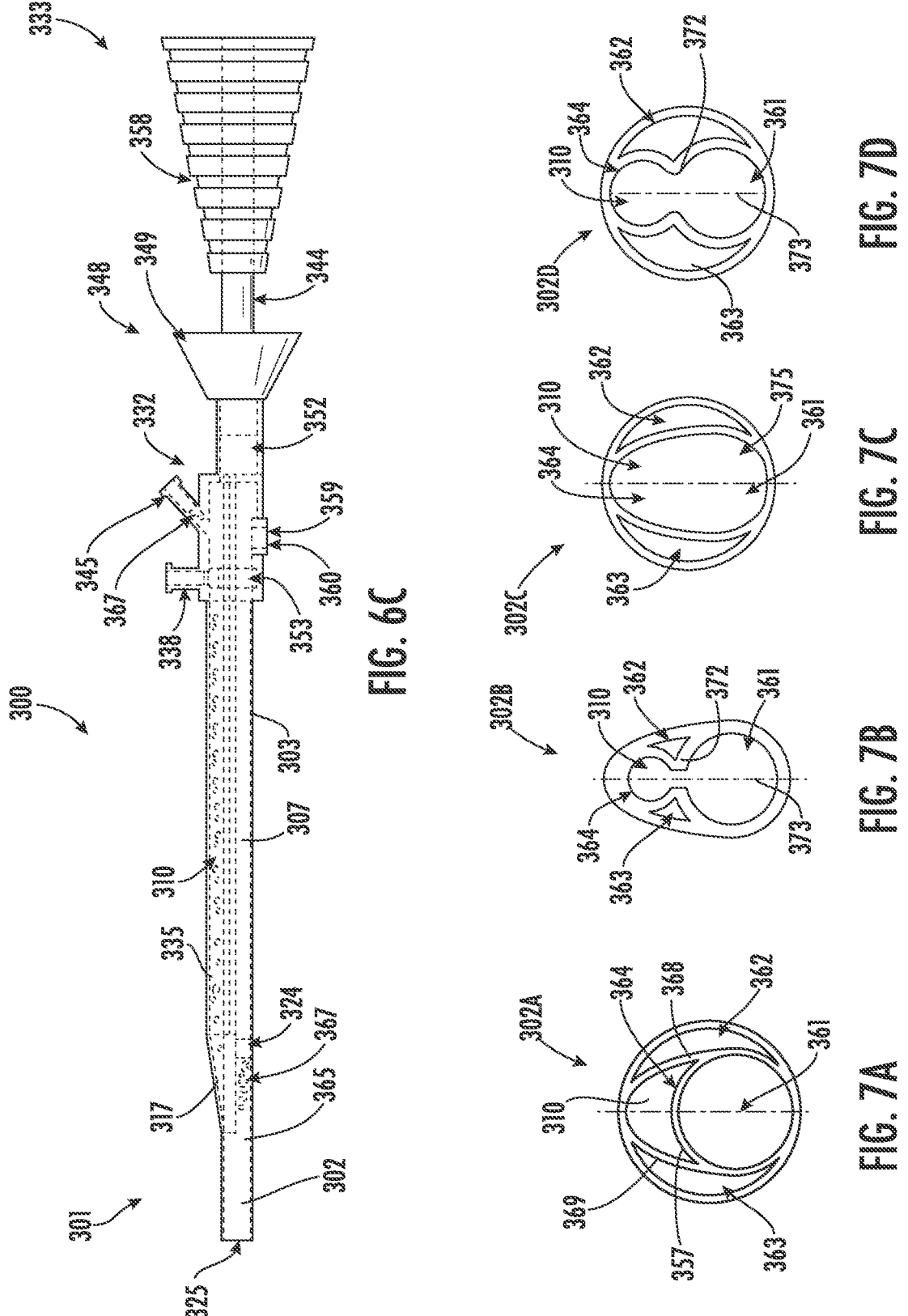
FIGS. 7A-7F depict end cross-sectional views of various sheaths of a medical device according to embodiments of the present disclosure.

Turning to FIGS. 6A-6C, a device 300 according to embodiments of the present disclosure will be described. It will be appreciated that the device 300 may share many similarities to the devices 100 and 200 described herein. As such, only certain aspects of the device 300 may hereinafter be described for the sake of brevity. A distal end 301 of the device 300 may include a sheath 302 and a scope 307 within a lumen defined by a wall 303 of the sheath 302, while a proximal end 333 of the device 300 may include a body 332 in fluid communication with the lumen of the sheath 302. The sheath 302 may have an ID that is slightly larger than the OD of the scope 307. In some embodiments, the scope 307 may include a laser 308 extending through a working channel thereof. As shown, the sheath 302 may further include a suction channel 310, which may be external or internal to the lumen of the sheath 302. The suction channel 310 may be in fluid communication with an inlet port 338 of the body 332.

As shown, the sheath 302 may further include an angled or tapered section 317 connecting the lumen of the sheath 302 with the suction channel 310. In some embodiments, a wall 335 defining the suction channel 310 may be joined, glued, heat flowed, or otherwise attached to a single flexible circular lumen tube of the sheath 302. The tapered section 317 may be angled or sloped between the suction channel 310 and the scope 307, which is beneficial to gauge the size of the stone dust between the taper slope and a distal end 324 of the scope 307.

As a result, dust size smaller than the gap therebetween is allowed to pass into or alongside the suction channel 310, as the distal end 324 of the scope 307 is moved proximally, to provide a smooth stone transport and to help prevent clogging as the dust is transported. The taper of the tapered section 317 can be gradual or stepped. When the scope 307 is advanced into a distal open-ended enclosure 365 of the sheath 302, the dust is blocked from entering the tapered section 317 and the suction channel 310.

In some embodiments, as demonstrated in FIGS. 6B-6C, the enclosure 365 can contain dust or fragments 367 for convenient containment, gathering, and storage for later removal. In some embodiments, the size/volume of the stone 366 can be viewed via the scope camera to determine, e.g., optimal volume removal and stone size passability. Fragments 367 can be popcorned for a longer duration to achieve a smaller dust size. During use, a distal end 325 of the sheath 302 can be extended or retracted relative to the distal end 324 of the scope 307. The scope 307 can be withdrawn further proximal within the sheath 302 to provide enclosure 365 with a deeper and larger volume, which helps prevent laser repulsed stone fragments 367 from escaping out the distal end 325 of the sheath 302. In some embodiments, the distal end 325 of the sheath 302 can be semi-rigid and may have a reinforced, cross-sectional profile to maximize allowable dust size passage and to maximize the ease of unclogging with a minimum outer profile. Furthermore, the distal end 325 of the sheath 302 may be mold tapered or taper trimmed in some embodiments to produce an atraumatic tip.

In this embodiment, fragments 367 may be suctioned out through the suction channel 310 while the distal end 324 of the scope 307 remains in place in the tapered section 317. Suction may be performed with or without the use of the scope camera. Alternatively, the scope 307 can be vacated or moved proximally in the scope 307 to allow for larger sized stone removal using the entire tapered section 317 via suction and/or to loosen dust clogs. In yet other embodiments, the scope 307 may be retracted to permit basketing through the sheath 302. The scope 307 may then be advanced distally for the next fragment under visualization. It will be appreciated that the scope 307 need not be entirely removed from the body 332 during suction, extraction, unclogging etc., of the suction channel 310. Instead, the distal end 324 of the scope 307 may only need to be moved proximal enough to allow the stone fragment to enter the enclosure 365 or exit a suction port 345 of the body 332. Alternatively, the scope 307 may be pulled proximally past the dust clog, voiding the once occupied space of the enclosure 365 to allow the clog to loosen and resolve. In some embodiments, a filter (not shown) may be positioned in line with the suction port 345 for stone collection. Once the fragments 367 are removed or unclogged, the scope 307 can again be advanced distally.

As further shown, the body 332 may include a rigid threaded cap 348 containing a through aperture and an elastic grommet 352. Proximal of the rigid threaded cap 348 may be a strain relief 358 of a scope handle (not shown). In some embodiments, the body 332 may further include a fitting 353 for coupling the sheath 302 to the body 332. As further shown in FIG. 6C, the rigid threaded cap 348 may include a funnel 349 for ease of insertion or reinsertion of the scope 307 should the shaft 344 be totally removed from the sheath 302 and/or the body 332. The distal end 324 of the shaft 344 of the scope 307 can also rest in the funnel 349 for easier reinsertion in some embodiments.

In some embodiments, the body 332 may include an aperture 359 enclosed by a slidable cover 360. The cover 360 can be operated manually to expose and seal the aperture 359. Covering the aperture 359 by the thumb or by the cover 360 ensures maximum suction, while fully uncovering the aperture 359 may minimize the suction. When an automated FMS is used, the 360 cover may be closed to ensure no fluid is lost or gained through the aperture 359.

FIGS. 7A-7F demonstrate cross-sectional views of the device 300 according to various embodiments of the present disclosure. As shown in FIG. 7A, the sheath 302A may include a first lumen 361 operable to receive the scope 307 (not shown), a second lumen 362 and a third lumen 363, which operate as inlet channels, and a fourth lumen 364, which corresponds to the suction channel 310. In some embodiments, the first lumen 361 is defined by a circular wall 357, the second lumen 362 is defined in part by a first longitudinal wall 368, and the third lumen 363 is defined in part by a second longitudinal wall 369. The fourth lumen 364 may be defined by the circular wall 357, the first longitudinal wall 368, and the second longitudinal wall 369.

As shown in FIG. 7B, the sheath 302B may include the first lumen 361 operable to receive the scope 307 (not shown), the second lumen 362 and the third lumen 363, which operate as inlet channels, and the fourth lumen 364, which corresponds to the suction channel 310. In this embodiment, the first lumen 361 and the fourth lumen 364 may not be fully separated by any wall, for example. Instead, the first lumen 361 and the fourth lumen 364 are fluidly connected, separated by a set of indentations 372 extending towards a centerline 373 of the sheath 302B. The set of indentations 372 may be provided to position the scope 307 within the first lumen 361, thus allowing more space for the suction channel 310.

As shown in FIG. 7C, the sheath 302C may include the first lumen 361 operable to receive the scope 307, the second lumen 362 and the third lumen 363, which operate as inlet channels, and the fourth lumen 364, which corresponds to the suction channel 310. In this embodiment, the first lumen 361 and the fourth lumen 364 are fluidly connected, without any walls or indentations positioned therebetween. Instead, a shape or profile of the first and second longitudinal walls 368, 369 may encourage positioning of the scope towards a bottom 375 of the first lumen 361. In this embodiment, the axis of first lumen 361 and the axis of the fourth lumen 364 are non-coaxial to maximize the height of the suction channel 310. During use, the scope 307 may be moved within the first lumen 361, e.g., for freeing space under a stone blockage to help increase fluid flow within the fourth lumen 364. Aspirating the fourth lumen 364 can also aid in the loosening of the clog. In yet other embodiments, a laser fiber of the scope 307 can also be reinserted into the first lumen 361 to fragment a clogged stone.

As shown in FIG. 7D, the sheath 302D may include the first lumen 361 operable to receive the scope 307, the second lumen 362 and the third lumen 363, which operate as inlet channels, and the fourth lumen 364, which corresponds to the suction channel 310. In this embodiment, the first lumen 361 and the fourth lumen 364 again are fluidly connected, separated by the set of indentations 372 extending towards the centerline 373. The set of indentations 372 may be provided to position the scope 307 within the first lumen 361. The sheath 302E of FIG. 7E is similar to FIG. 7D except for a set of ribs 378 extending from the first and second longitudinal walls 368, 369 to position the scope within the first lumen 361.

Figures 7E, 7F:
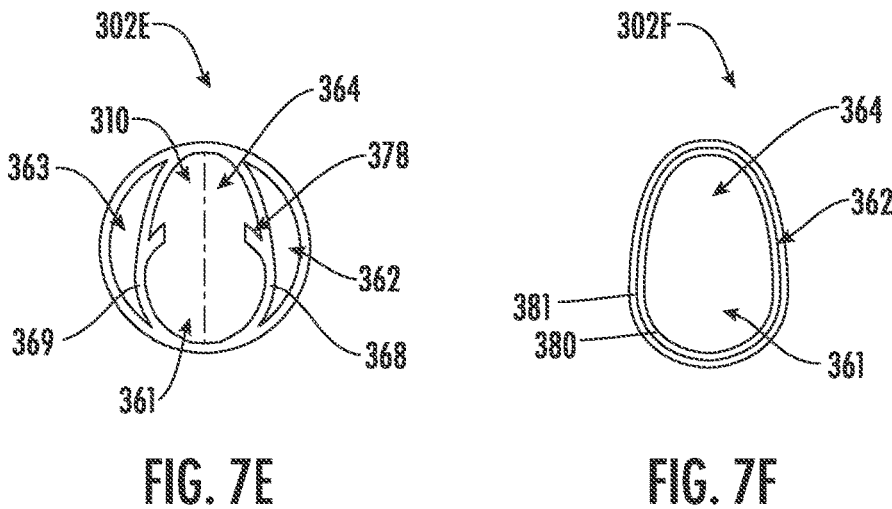

As shown in FIG. 7F, the first and fourth lumens 361, 364 of sheath 302F are fluidly connected, with the second lumen 362 positioned between an inner wall 380 and an outer wall 381. In this embodiment, the inner and outer walls 380, 381 are co-axially positioned, which may be particularly advantageous for micro dust or finer stone particles.

Figure 8:
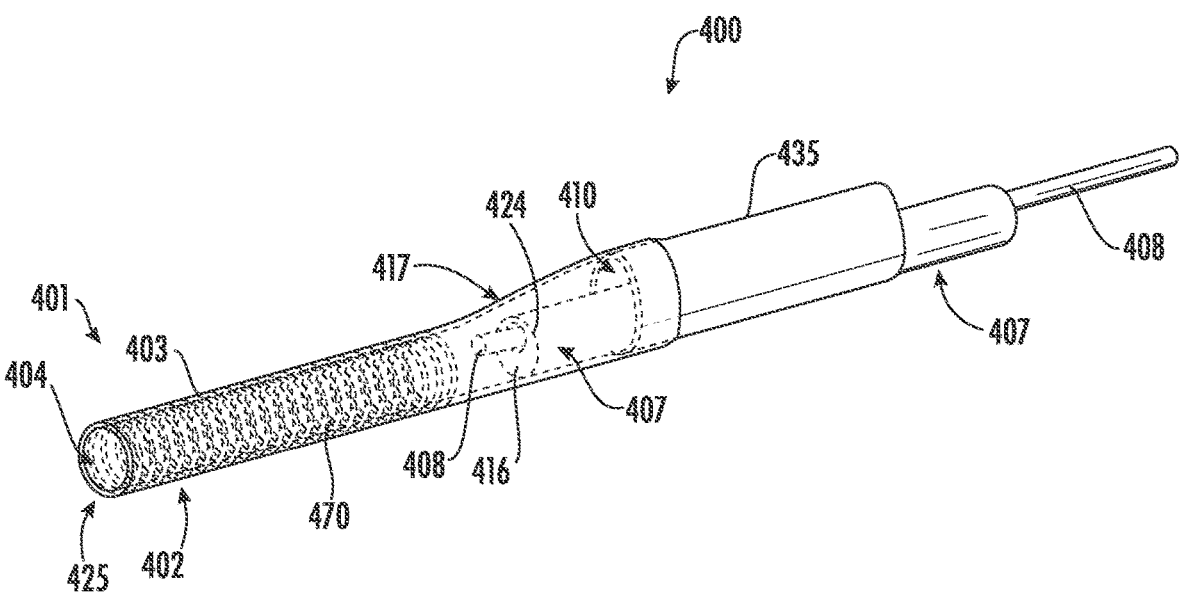
FIG. 8 depicts a perspective view of a distal portion of a medical device according to embodiments of the present disclosure.

Turning to FIG. 8, a device 400 according to embodiments of the present disclosure will be described. As shown, a distal end 401 of the device 400 may include a sheath 402 having a wall 403 defining a first lumen 404. A scope 407 may extend through the first lumen 404, the scope 407 including a laser 408 (e.g., fiber) extending through a working channel thereof. The laser 408 can be exposed or extended from the scope 407 and/or sheath 402 to fragment/dust renal stones upon impact, as described above. The scope 407 may include a visualization device 416 (e.g., a camera) located along a distal end 424 of the scope 407. In some embodiments, the device 400 may include an angled or tapered section 417 extending to a wall 435. The tapered section 417 and the wall 435 may define a suction channel 410 positioned above the scope 407. In this embodiment, the sheath 402 may be reinforced, e.g., with a helical coil 470 extending to a distal end 425 of the sheath 402. In non-limiting embodiments, the helical coil 470 may be made from a polymer or a metal.

Figures 9A, 9B:
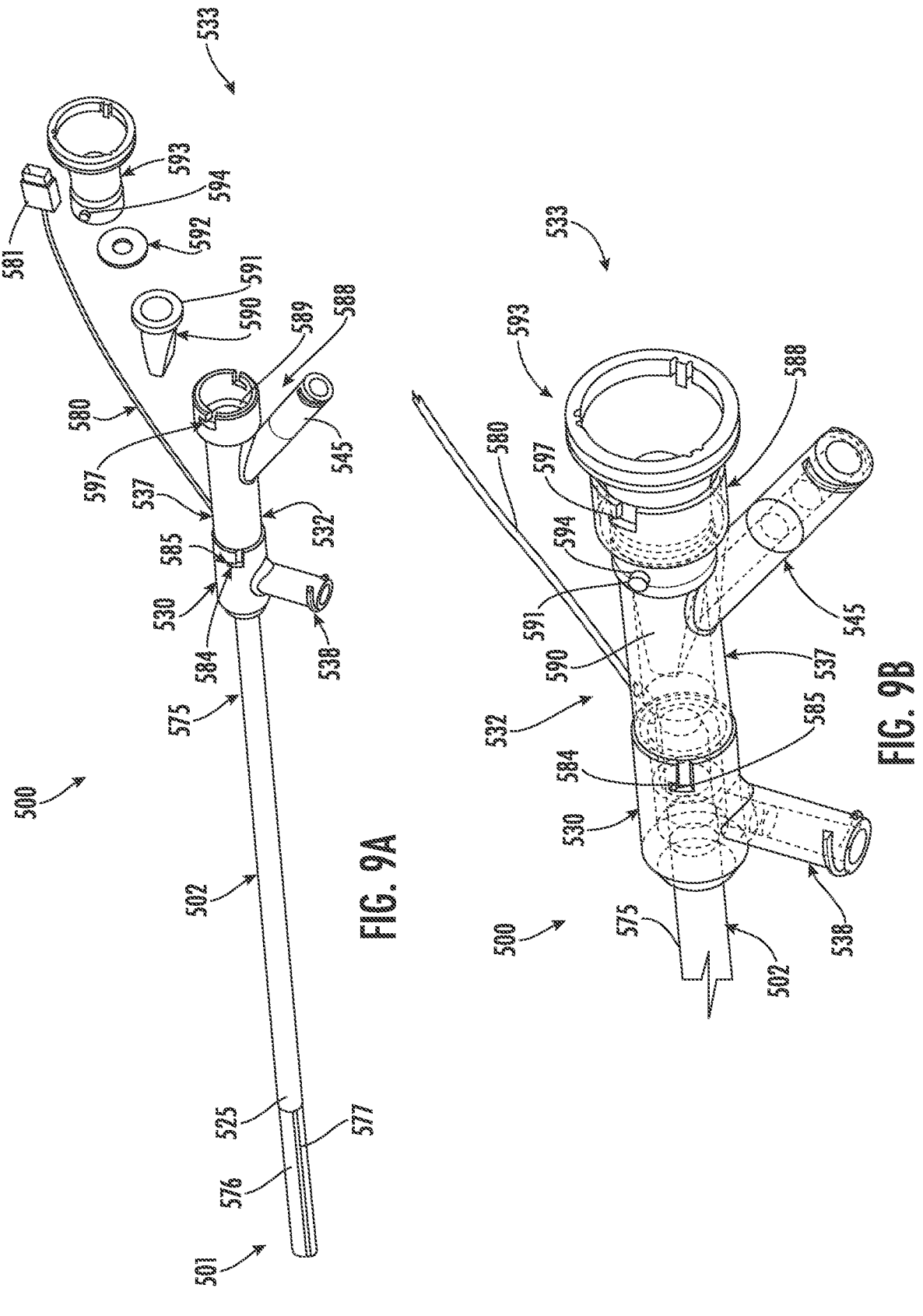
FIG. 9A depicts a perspective view of a medical device according to embodiments of the present disclosure.
FIG. 9B depicts a perspective view of a body of the medical device of FIG. 9A according to embodiments of the present disclosure.
Figures 10A, 10B, 10C, 10D, 10E, 10F, 10G, 10H:
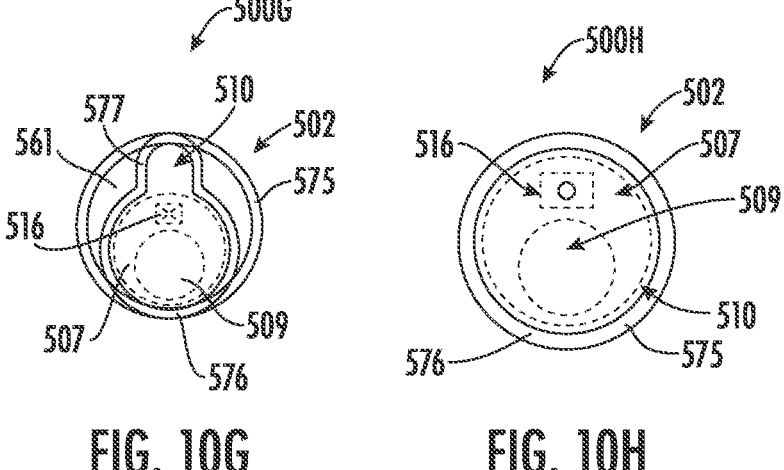
FIGS. 10A-10H depict end cross-sectional views of various sheaths of a medical device according to embodiments of the present disclosure.

FIGS. 9A-9B demonstrate a device 500 according to embodiments of the present disclosure. It will be appreciated that the device 500 may share many similarities to the devices 100, 200, and 300 described herein. As such, only certain aspects of the device 500 may hereinafter be described for the sake of brevity. A distal end 501 of the device 300 may include a sheath 302 and a scope (not shown) within a lumen defined by one or more walls of the sheath 502. A proximal end 533 of the device 500 may include a body 532, which is in fluid communication with one or more lumens of the sheath 502. In this embodiment, the sheath 502 may include an outer tube 575 surrounding a scope tube 576 and a suction tube 577. Although not shown, the scope tube 576 may contain the scope, while the suction tube 577 may define a suction channel. In some embodiments, the scope tube 576 and the suction tube 577 may extend beyond a distal end 525 of the outer tube 575.

As further shown, the body 532 may include an inlet body 530 coupled to an outlet body 537. In some embodiments, a pin 584 and a slot 585 may be used to couple the inlet body 530 and the outlet body 537 together. It will be appreciated that the inlet body 530 and the outlet body 537 may be coupled together using a variety of different approaches, however. As shown, the sheath 502 may extend through the inlet body 530, which includes an inlet port 538. Also extending through the body 532 is a sensor lead 580 and connector 581, which may be used to measure and communicate pressure, temperature, force, etc.

The outlet body 537 may further include a suction port 545 adjacent a fitting 588, which includes seat 589, and a valve 590 having a rim 591, wherein the rim 591 is configured to engage the seat 589. The outlet body 537 may further include a washer 592 and a navigator funnel 593. As shown, the navigator funnel 593 may include a pin 594 configured to enter a slot or channel 597 of the fitting 588 to hold the components together.

Turning now to FIGS. 10A-10H, cross-sectional views of various devices 500A-500I according to embodiments of the disclosure will be described. As shown, the sheath 502 includes the outer tube 575, the scope tube 576, and the suction tube 577. One or more inlet channels 561 may be formed between the outer tube 575 and the scope tube 576 and/or the suction tube 577. In some embodiments, the suction tube 577 may define a suction channel 510 through the sheath 502. A scope 507 may extend through the scope tube 576, the scope 507 including a camera 516 and a lumen 509 (e.g., a working channel) for a laser.

Figures 11A, 11B, 11C, 11D, 11E:
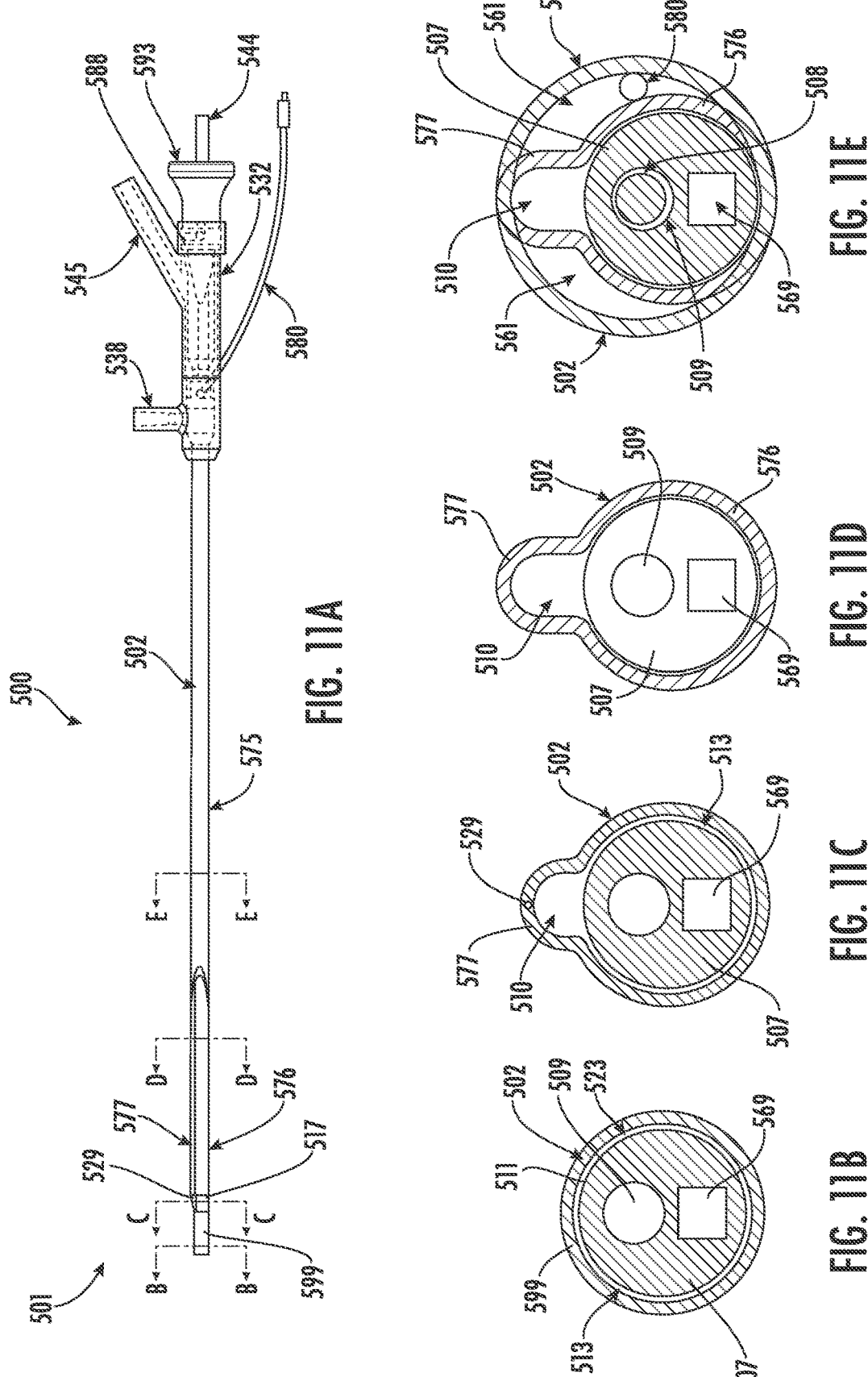
FIG. 11A depicts a side view of a medical device according to embodiments of the present disclosure.
FIG. 11B depicts an end cross-sectional view of the medical device of FIG. 11A along cutline B-B, according to embodiments of the present disclosure.
FIG. 11C depicts an end cross-sectional view of the medical device of FIG. 11A along cutline C-C, according to embodiments of the present disclosure.
FIG. 11D depicts an end cross-sectional view of the medical device of FIG. 11A along cutline D-D, according to embodiments of the present disclosure.
FIG. 11E depicts an end cross-sectional view of the medical device of FIG. 11A along cutline E-E, according to embodiments of the present disclosure.

FIGS. 11A-11E demonstrate the device 500 according to another embodiment of the present disclosure. As shown in FIG. 11B, which is a cross-section of a distal tip 599 of the sheath 502 taken along cutline B-B of FIG. 11A, the scope 507 extends centrally through a lumen 513 defined by the distal tip 599. In some embodiments, an interior of the distal tip 599 of the sheath 502 represents a fragmentation chamber operable to fragment a bodily mass. The scope 507 may include a camera lumen 569 for a camera (not shown) and the lumen 509 for the laser. In some embodiments, the lumen 509 represents a working channel of the scope 507. Between an exterior surface 511 of the scope 507 and an interior surface of the distal tip 599 of the sheath 502 is a suction gap or passageway 523. As shown in FIG. 11C, which is a cross-section of a tapered section 517 of the sheath 502 taken along cutline C-C of FIG. 11A, the suction channel 510 begins to appear above the scope 507. The suction channel 510 may be defined by a sloped wall 529 of the suction tube 577. As shown in FIG. 11D, which is a cross-section of the sheath 502 taken along cutline D-D of FIG. 11A, the scope 507 and the suction channel 510 further extend through the suction tube 577 and the scope tube 576.

As shown in FIG. 11E, which is a cross-section of the sheath 502 taken along cutline E-E of FIG. 11A, the scope 507, the suction channel 510, the suction tube 577, and the scope tube 576 extend through the outer tube 575. In this embodiment, the scope tube 576, the suction tube 577 and the outer tube 575 define the inlet channels 561. As further shown, the sensor lead 580 may extend between the scope tube 576 and the outer tube 575. The laser 508 is demonstrated within the lumen 509.

In another embodiment, the sheath 502 may be a flexible, thin wall. A space between an inner surface of the wall of the sheath 502 and an exterior of the scope 507 may be used for inlet fluid flow. The working channel (lumen 509) of the scope 507, which includes the laser, may be used as a suction channel. In this embodiment, the fragmentation chamber may be the working channel, at the distal end of the scope 507. A tip of the laser may be retracted into the working channel to fragment a bodily mass therein. In some embodiments, the working channel of the scope 507 has a larger area than the inlet lumen for suctioning out dust/fragments from the bodily mass.

Figure 12A:
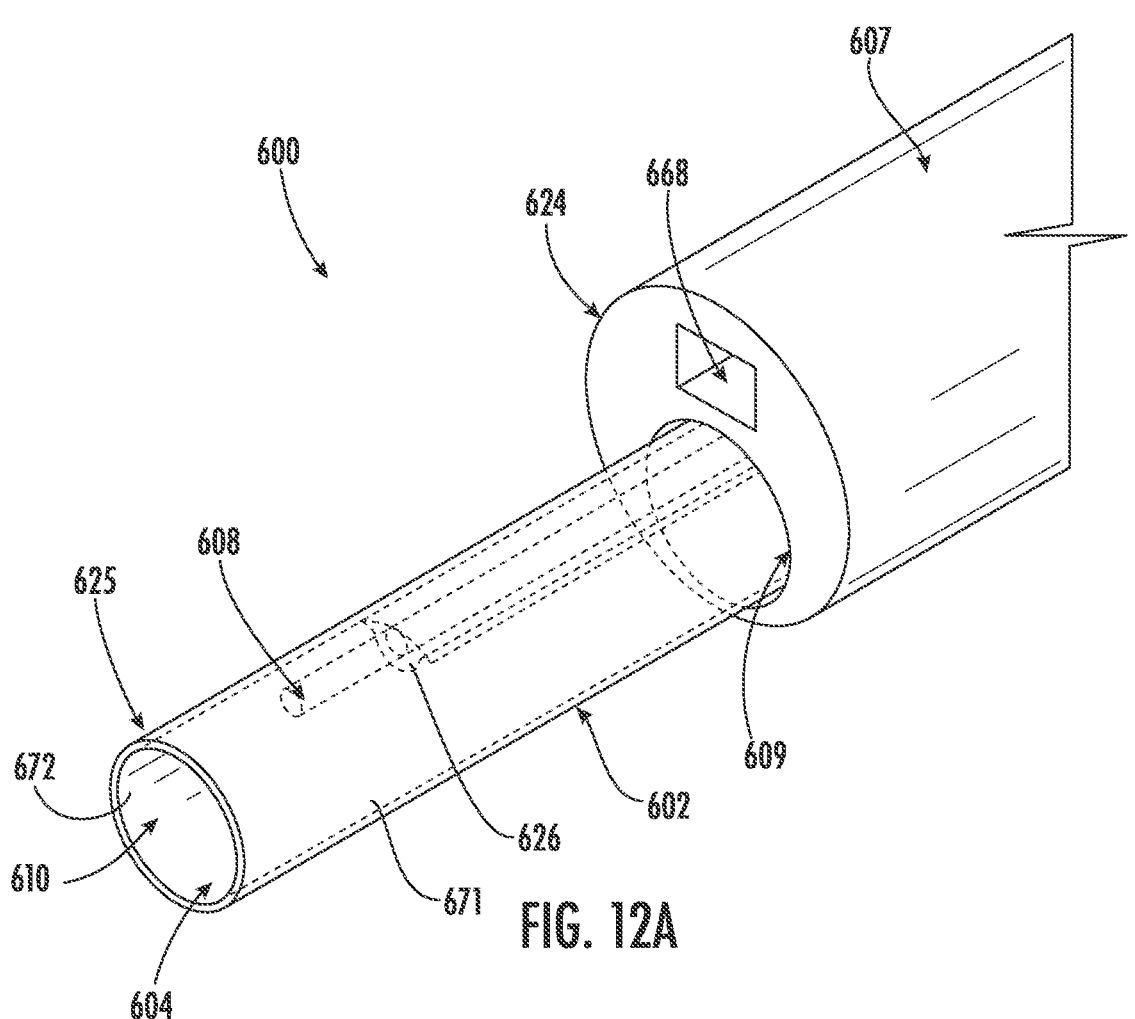
FIG. 12A depicts a perspective view of a distal portion of a medical device according to embodiments of the present disclosure.
Figure 12B:
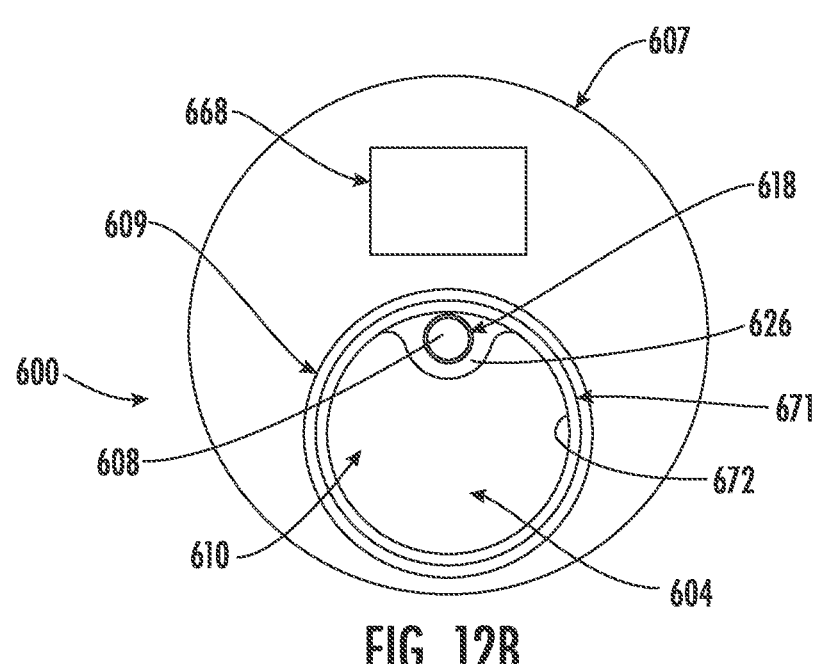
FIG. 12B depicts an end cross-sectional view of the medical device of FIG. 12A according to embodiments of the present disclosure.

Turning now to FIGS. 12A-12B, a portion of a device 600 according to embodiments of the present disclosure will be described. As shown, the device 600 may include a scope 607 having a lumen 668 for a camera and/or a pressure sensor, and a working channel 609 for a sheath 602. The sheath 602 may include a wall 603 extending beyond a distal end 624 of the scope 607, wherein the wall 603 includes an outer wall or surface 671 and an internal wall or surface 672. The internal surface 672 may define a suction channel 610 of a first lumen 604 of the sheath 602. As shown, a laser 608 extends through the first lumen 604 of the sheath 602 and through the working channel 609 of the scope 607. More specifically, the laser 608 may extend through a second lumen 618 defined by a laser housing 626. As shown, the laser housing 626 may generally extend from the internal surface 672 of the sheath 602 to maintain the laser 608 to one side of the suction channel 610, thus allowing a larger area for stone dust removal. In other embodiments, no laser housing 626 is provided, and the laser 608 may simply extend through the first lumen 604 of the sheath 602. In some embodiments, the first lumen 604 may represent a fragmentation chamber operable to fragment a bodily mass using the laser 608. The laser 608 and/or the sheath 602 may move axially (e.g., in and out of the working channel 609) relative to the distal end 624 of the scope 607.

During use, larger stones may be brought by suction to a distal end 625 of the sheath 602 for fragmentation by the laser 608. Smaller stones and/or stone dust entering the sheath 602 may be further fragmented by the laser 608 and brought into the scope 607 through the working channel 609 for removal.

Figure 13:
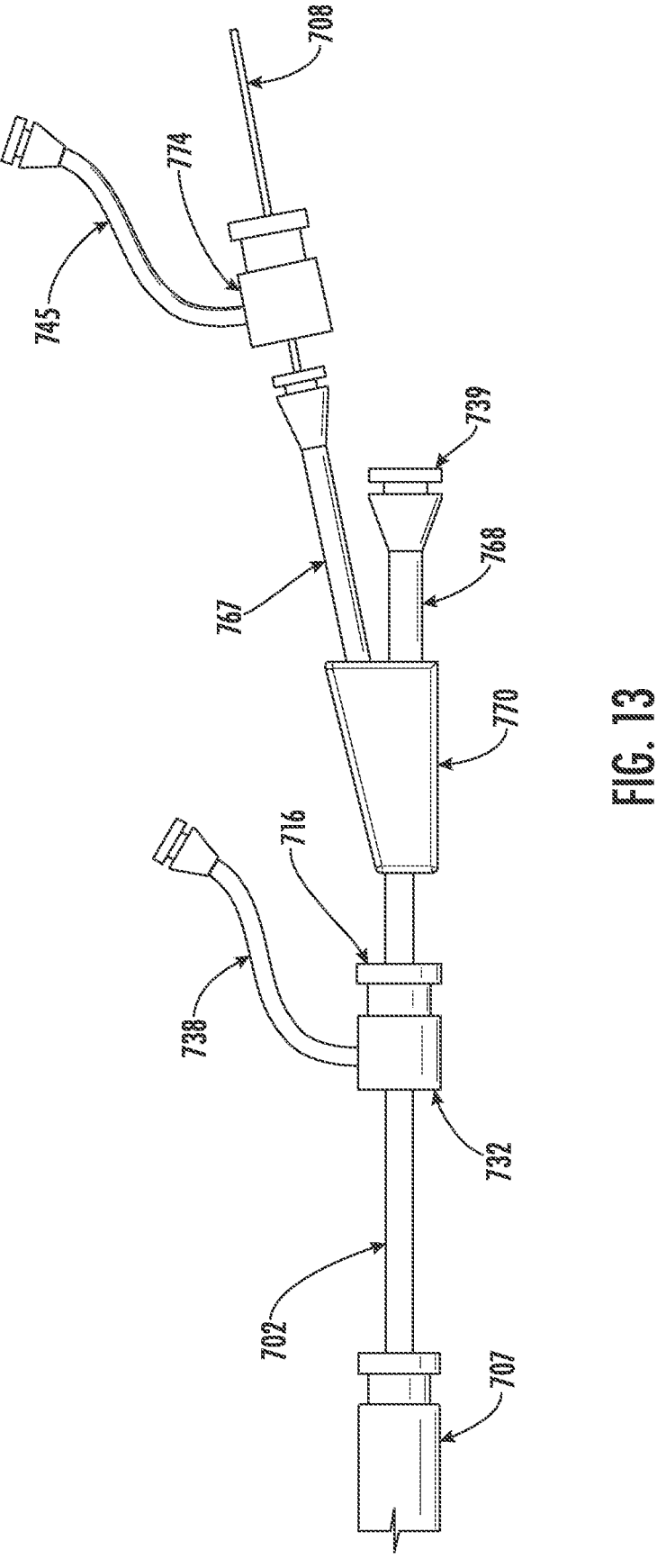
FIG. 13 depicts a side view of a proximal portion of a medical device according to embodiments of the present disclosure.

FIG. 13 demonstrates a proximal portion of a device 700 according to embodiments of the present disclosure. As shown, the device 700 may include a sheath 702 extending through a scope 707. The sheath 702 may further extend through a body 732 including a valve 716. The body 732 may include an inlet port 738, which is a fluid inlet between the scope 707 and the sheath 702. In some embodiments, the device 700 may further include a bifurcation device 770 coupling together a laser tube 767 and a suction tube 768. The laser tube 767 may surround or house a laser fiber 708. In some embodiments, the laser fiber 708 extends through a self-closing valve 774, which may include a suction port 745. The suction tube 768 may include a fitting 739 for connection with a filter or drain line (not shown).

Figure 14A:
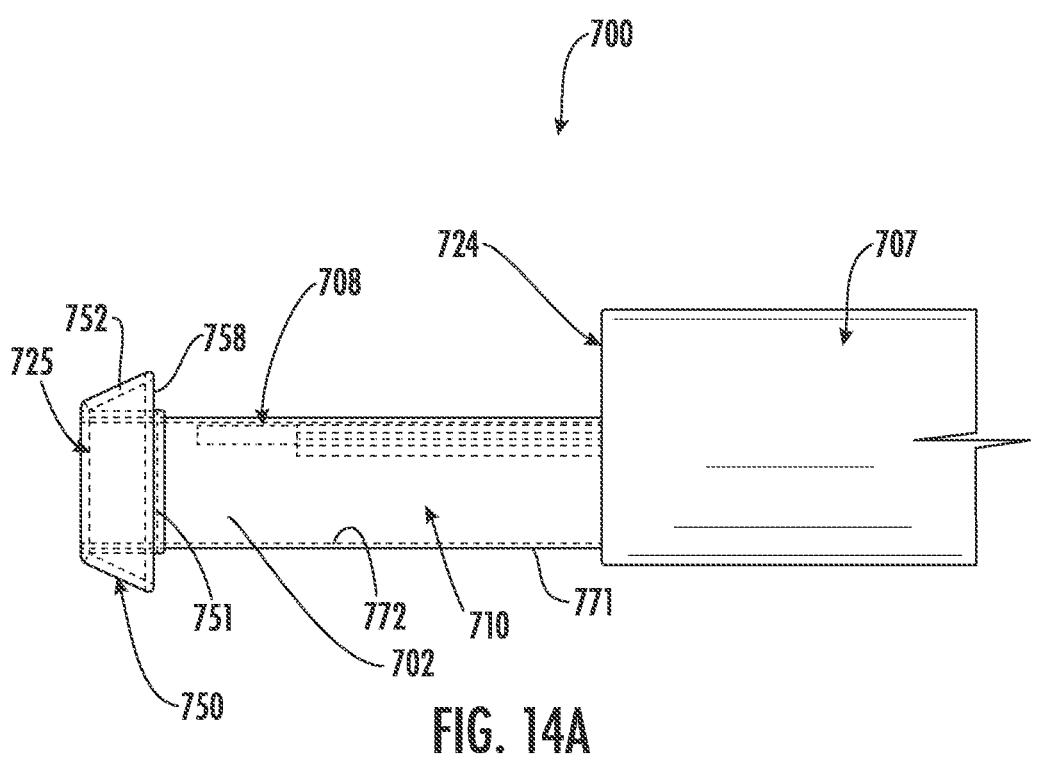
FIGS. 14A-14B depict side views of various distal portions of the medical device of FIG. 13 according to embodiments of the present disclosure.
Figure 14B:
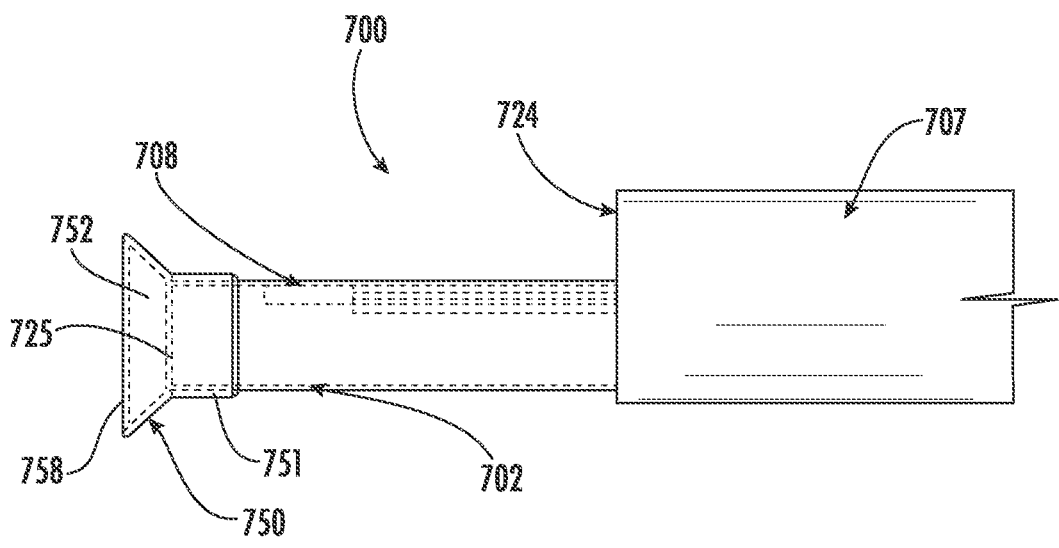

Turning now to FIGS. 14A-14B, a distal portion of the device 700 according to various embodiments of the present disclosure will be described. As shown, the device 700 may include the sheath 702 extending beyond a distal end 724 of the scope 707. The sheath 702 may include an outer wall or surface 771 and an internal wall or surface 772. The internal surface 772 may define a suction channel 710. As shown, the internal surface 772 may surround the laser 708. During use, stones and/or stone dust entering at a distal end 725 of the sheath 702 may be fragmented by the laser 708. In this embodiment, the laser 708 may be coupled to the internal surface 772 of the sheath 702 to maintain the laser 708 to one side of the suction channel 710, thus allowing a larger area for stone dust removal.

Attached to the distal end 725 of the sheath 702 is an attachment or cap 750. The cap 750 may further define a fragmentation chamber of the sheath 702. As shown, the cap 750 may include a first section 751 that extends around the outer surface 771 of the sheath 702, and a second section 752 extending from the first section 751. As shown, the second section 752 flares outwardly from the outer surface 771 of the sheath 702. In the embodiment of FIG. 14A, the second section 752 may extend towards the scope 707, partially overlapping the first section 751. In the embodiment of FIG. 14B, the second section 752 extends away from the scope 707. Said another way, a rim 758 of the second section 752 may be either proximally or distally positioned relative to the distal end 725 of the sheath 702. During use, the cap 750 may act as a funnel for stones and/or stone dust. Furthermore, the stones and/or stone dust can be popcorned within the cap 750 upon impact by the laser 708, thus causing repeated fragmentation.

Figure 15A:
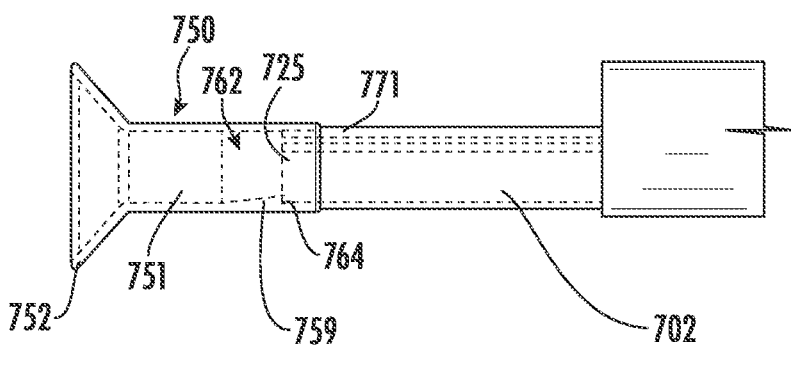
FIG. 15A depicts a side view of an attachment for a medical device according to embodiments of the present disclosure.
Figure 15B:
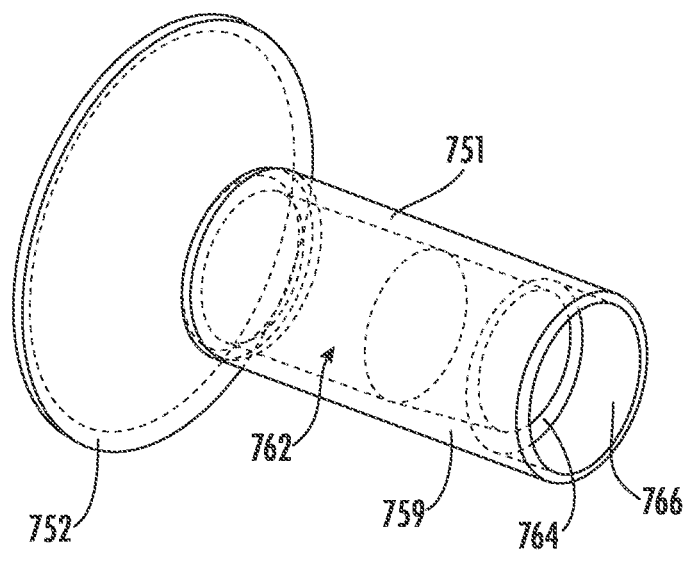
FIG. 15B is a perspective view of the attachment of FIG. 15A according to embodiments of the present disclosure.

In FIGS. 15A-15B, the first section 751 of the cap 750 may be elongated relative to the second section 752. As shown, the first section 751 may include a tapered surface 759, which functions as a sizer for the stones and/or stone dust within a lumen 762 of the cap 750. The tapered surface 759 reduces an internal area of the lumen 762 defined by the first section 751 proximate the sheath 702. In some embodiments, the first section 751 includes a stopping surface 764 configured to abut a distal face of the distal end 725 of the sheath 702 when an interior surface 766 of the cap 750 surrounds the outer surface 771 of the sheath 702.

Figure 16:
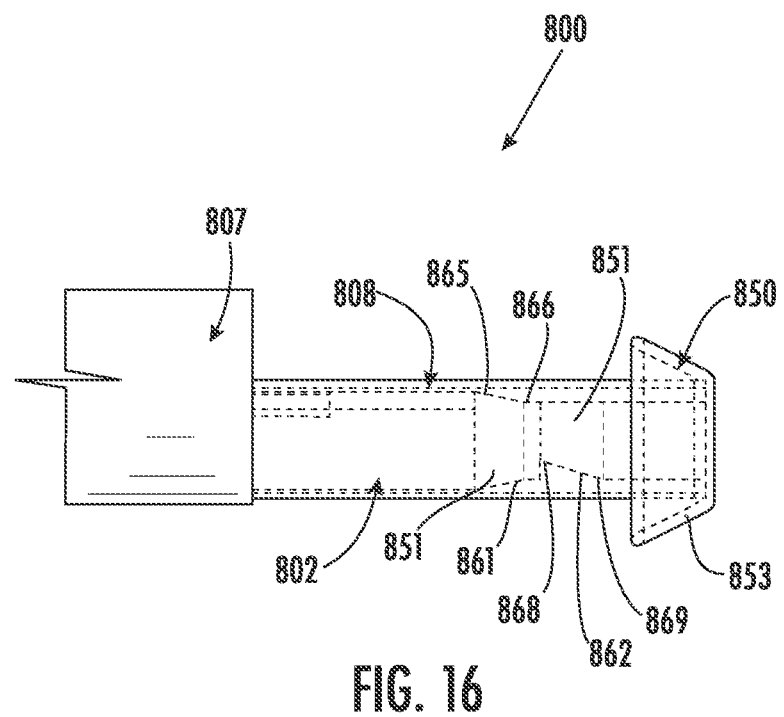
FIG. 16 depicts a side view of an attachment for a medical device according to embodiments of the present disclosure.

In FIG. 16, a device 800 may include an attachment or cap 850 partially inserted within an interior of a sheath 802. The cap 850 may further define a fragmentation chamber of the sheath 802. In this embodiment, the cap 850 may include a first section 851 directly adjacent a laser 808. The first section 851 may include a first surface 861, which slopes or tapers towards an interior lengthwise axis (not shown) of the sheath 802. That is, the first surface 861 may have a proximal end 865 opposite a distal end 866, wherein a diameter or cross-sectional area of the first section 851 at the distal end 866 is less than a diameter or cross-sectional area of the first section 851 at the proximal end 865.

The cap 850 may further include a second section 852 having a second surface 862, which slopes or tapers away from the interior lengthwise axis of the sheath 802. Said another way, a diameter or interior area of the second section 852 at a proximal end 868 of the second surface 862 is less than a diameter or cross-sectional area of the second section 852 at a distal end 869. Extending from the second section 852 is a third section 853. In this embodiment, the third section 853 extends back towards a scope 807, forming an inverted funnel. In other embodiments, the third section 853 may extend away from the scope 807.

Figure 17:
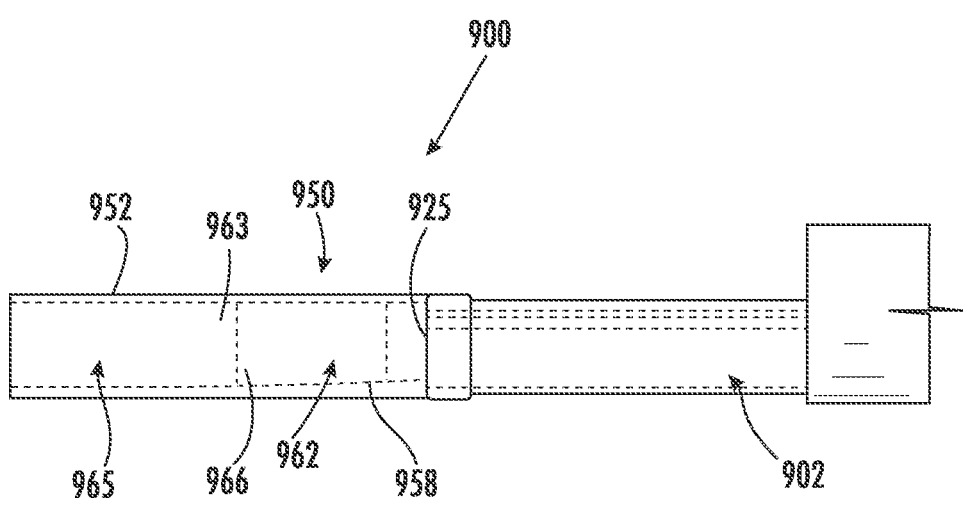
FIG. 17 depicts a side view of an attachment for a medical device according to embodiments of the present disclosure.

In FIG. 17, a device 900 may include a cap 950 secured around an exterior of a sheath 902. The cap 950 may include a first section 951 having an internal tapered surface 958, which functions as a sizer for the stones and/or stone dust. As shown, the tapered surface 958 reduces an internal area of a lumen 962 defined by the first section 951 proximate the sheath 902. In some embodiments, the first section 951 includes a stopping surface 964 configured to abut a distal face of a distal end 925 of the sheath 902. The first section 951 is connected with a second section 952. As shown, the first and second sections 951, 952 are fluidly connected. In some embodiments, a proximal side 963 of the second section 952 may have a same or similar diameter as a distal side 966 of the first section 951. The second section 952 may be elongated along an interior lengthwise axis to provide a distal open-ended enclosure 965. The enclosure 965 can contain dust or fragments for convenient containment, fracturing, and storage for later removal.

Figure 18:
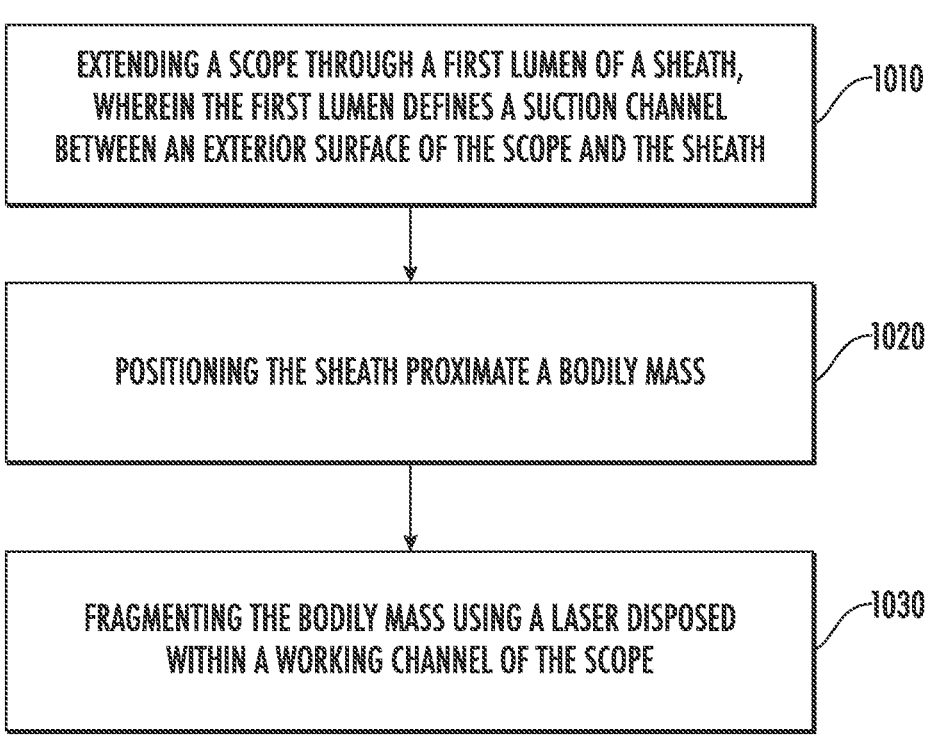
FIG. 18 is a flow diagram of a method according to embodiments of the present disclosure.

Turning now to FIG. 18, a method 1000 according to embodiments of the present disclosure will be described. At block 1010, the method 1000 may include extending a scope through a first lumen of a sheath, wherein the first lumen defines a suction channel between an exterior surface of the scope and the sheath. In some embodiments, the wall of the sheath may further define a second lumen. In some embodiments, a pressure sensor may extend through the second lumen. In some embodiments, the wall of the sheath may further define a third lumen, wherein the pressure sensor extends through the third lumen. In some embodiments, the sheath may include a fluid opening extending through the wall of the sheath. In some embodiments, the fluid opening extends into the second lumen. In some embodiments, the sheath further includes an angled tip extending from a distal end, wherein the pressure sensor extends into the angled tip. In some embodiments, the pressure sensor extends through a tip opening in an outer surface of the angled tip, wherein the angled tip includes a tip lumen and a suction chamber, and wherein the suction channel, the second lumen, and the suction chamber are in fluid communication. In some embodiments, an attachment may be coupled to the distal end of the sheath, the attachment including a flared section. In some embodiments, the attachment may include a tapered internal surface. In some embodiments, the scope may further include a camera disposed along a distal face. In some embodiments, the scope is radially offset with respect to an approximate center of the first lumen. In some embodiments, the sheath further includes a skive hole at a proximal end for entry of a fluid and exit of a lead wire.

At block 1020, the method 1000 may include positioning the sheath proximate a bodily mass. In some embodiments, the sheath may be brought into position manually. In some embodiments, the sheath is brought into position with the aid of a visualization device coupled to or extending through the scope. In some embodiments, the bodily mass is drawn towards the sheath by a suction force.

At block 1030, the method 1000 may further include fragmenting the bodily mass using a laser disposed within a working channel of the scope. In some embodiments, the laser is a laser fiber configured to extend past the distal end of the scope. The laser may repeatedly impact the bodily mass to break the bodily mass into smaller and smaller portions. In some embodiments, a suction may be applied via the suction channel to position the bodily mass against a distal end of the sheath. The bodily mass may then be fragmented while the bodily mass is positioned against the distal end of the sheath. Once the bodily mass, or portions of the bodily mass, are small enough, they are drawn into the distal end of the sheath. In some embodiments, the bodily mass may continue to be fragmented by the laser while contained within the first lumen of the scope. The fragmented bodily mass may then be removed via the suction channel of the sheath.

The processes described in blocks 1020 and 1030 may be repeated as many times as desired to break up and remove the bodily mass from treatment site. Furthermore, the sheath may be repositioned as many times as necessary. Once the bodily mass and/or other material has been removed from the treatment site, which may be confirmed via camera and/or illumination source or other methods, the operator may remove the device from the treatment site.

Figure 19:
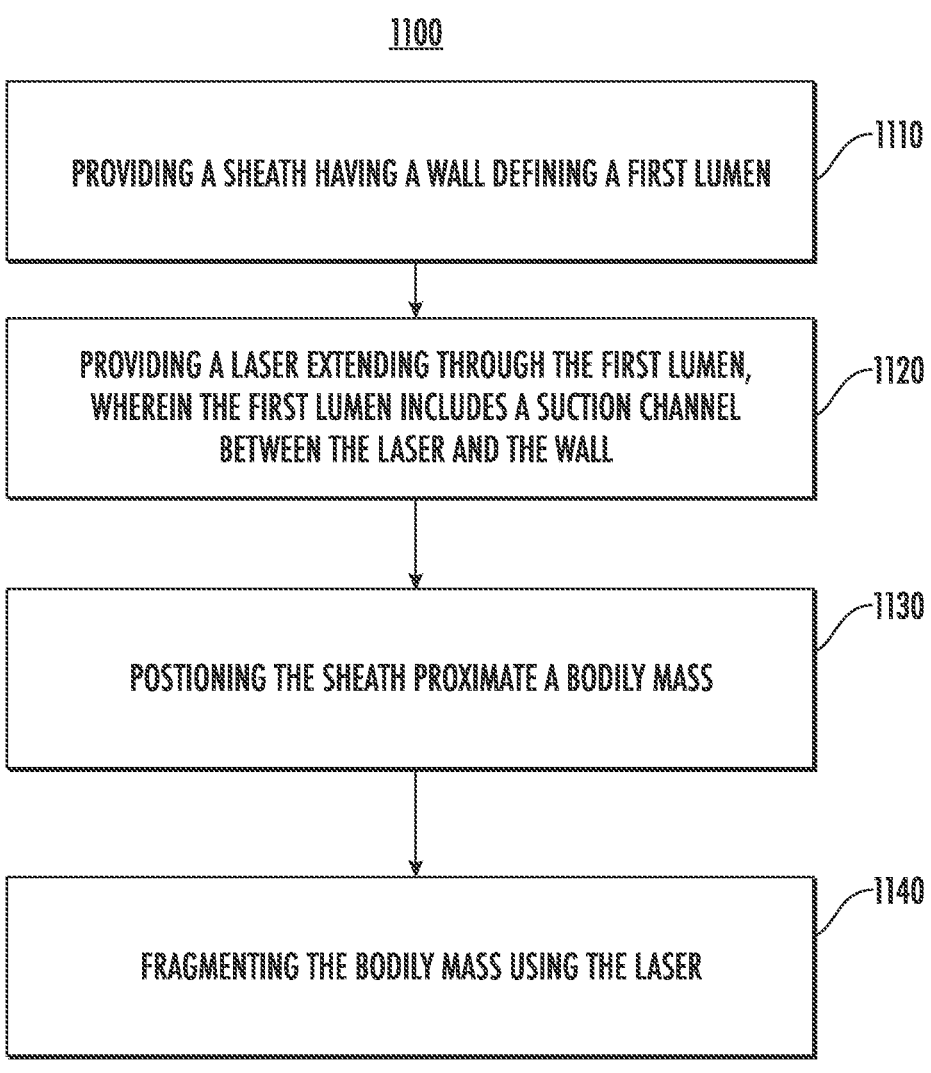
FIG. 19 is a flow diagram of a method according to embodiments of the present disclosure.

Turning now to FIG. 19, a method 1100 according to embodiments of the present disclosure will be described. At block 1110, the method 1100 may include providing a sheath having a wall defining a first lumen. At block 1120, the method 1100 may include providing a laser extending through the first lumen, wherein the first lumen includes a suction channel between the laser and the wall. In some embodiments, the laser is delivered through a second lumen defined by a laser housing extending from, or connected with, an internal surface of the wall of the sheath. In some embodiments, the suction channel is located between the laser housing and the internal surface of the wall of the sheath.

In some embodiments, the method may include delivering the laser through a working channel of a scope. In some embodiments, the sheath extends through the working channel of the scope. In some embodiments, the scope is positioned within the first lumen of the sheath.

At block 1130, the method 1100 may include positioning the sheath proximate a bodily mass. In some embodiments, the scope may include one or more feedback devices (e.g., cameras) to aid with sheath positioning. At block 1140, the method may include fragmenting the bodily mass using the laser. In some embodiments, suction may be applied via the suction channel to position the bodily mass against a distal end of the sheath. The bodily mass may then be fragmented while the bodily mass is positioned against the distal end of the sheath. In some embodiments, the method 1100 may further include applying a suction via the suction channel to draw the bodily mass within the distal end of the sheath, and fragmenting the bodily mass while the bodily mass is positioned within the distal end of the sheath.

In some embodiments, the method 1100 may further include providing a fluid opening through a wall of the sheath, and delivering a fluid from the fluid opening to a suction chamber extending from the distal end of the sheath. The fluid may then be delivered from the suction chamber to the suction channel.

The processes described in blocks 1130 and 1140 may be repeated as many times as desired to break up and remove the bodily mass from treatment site. Furthermore, the sheath may be repositioned as many times as necessary. Once the bodily mass and/or other material has been removed from the treatment site, which may be confirmed via camera and/or illumination source or other methods, the operator may remove the device from the treatment site.

Figures 20A, 20B:
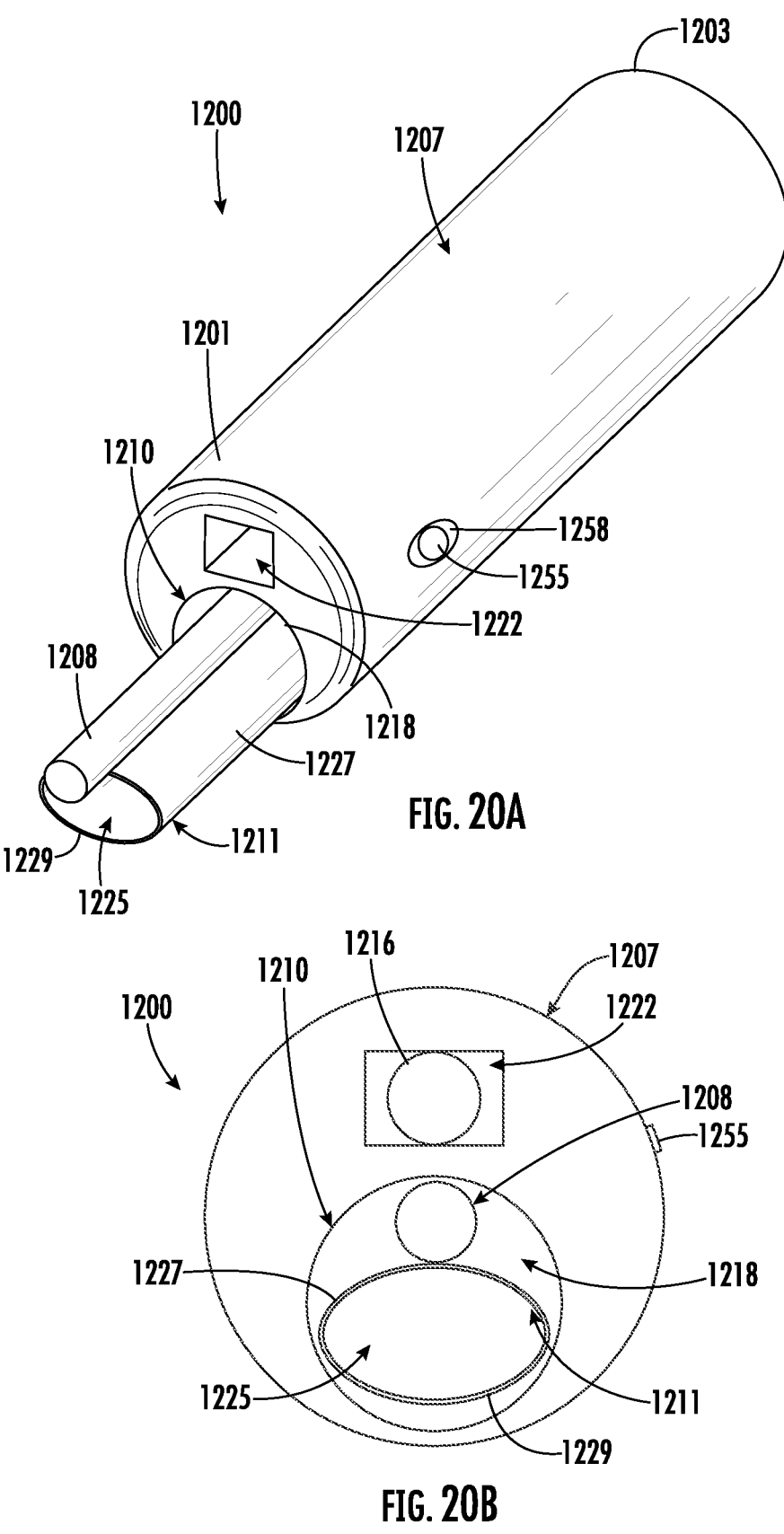
FIG. 20A is a perspective view of a distal portion of a medical device according to embodiments of the present disclosure.
FIG. 20B is an end cross-sectional view of the medical device of FIG. 20A according to embodiments of the present disclosure.
Figure 20C:
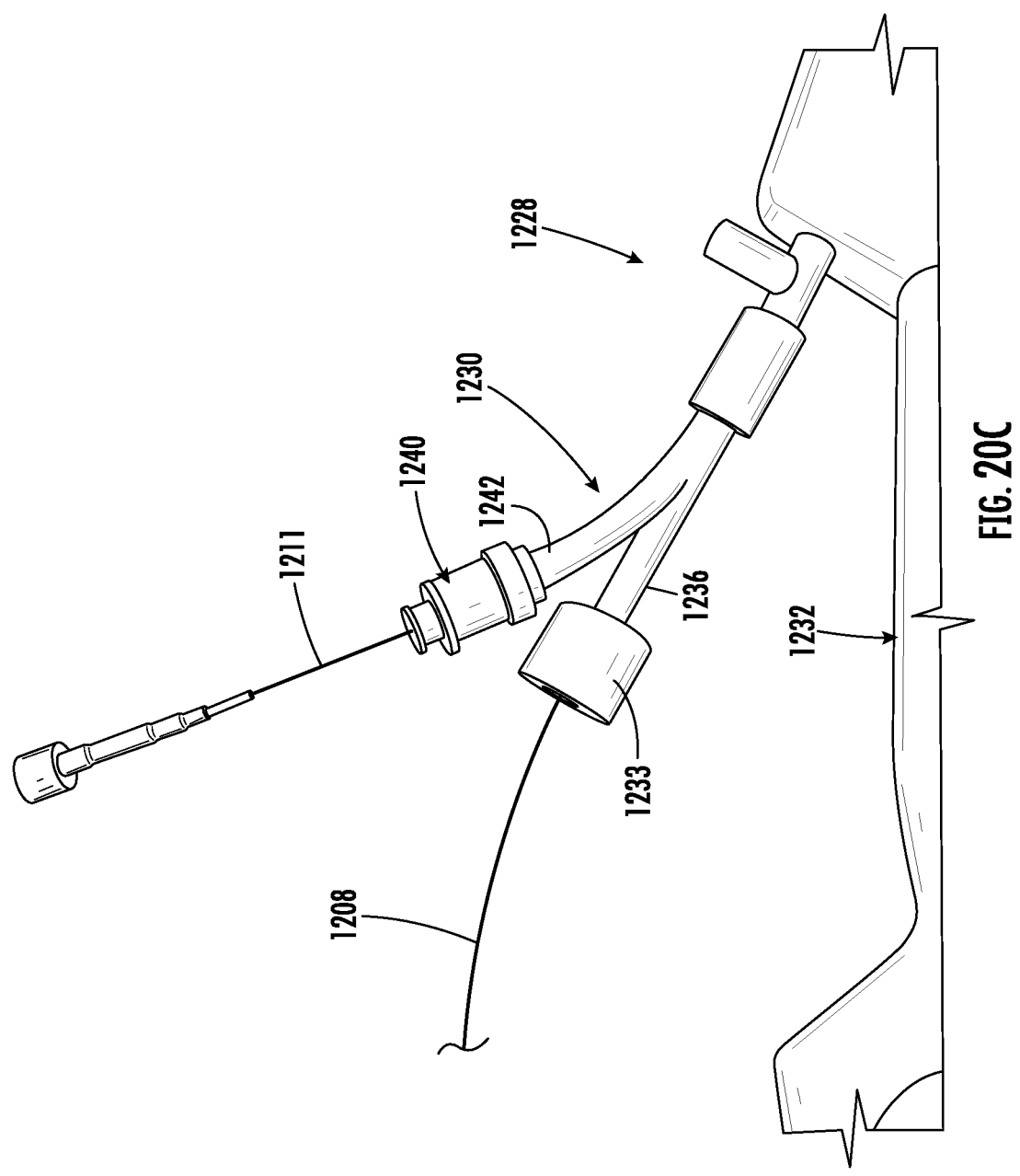
FIG. 20C is a perspective view of a handle for use with the medical device of FIGS. 20A-20B according to embodiments of the present disclosure.

Turning now to FIGS. 20A-20C, a portion of a device 1200, such as a suction evacuation assembly or system, will be described. As shown, the device 1200 may include a scope 1207 having a distal end 1201 opposite a proximal end 1203. The proximal end 1203 may be connected to a deployment device 1228, as shown in FIG. 20C, which may include a handle section 1232 and a gateway or Y-connector 1230. During use, insertion of a laser 1208 (e.g., laser fiber) and a sheath 1211 may occur through the Y-connector 1230. In some embodiments, the Y-connector may include a Tuohy Borst adapter 1233 positioned in a first leg 1236 to prevent the backflow of fluid around the laser 1208. A self-closing seal 1240 may be provided in a second leg 1242 of the Y-connector, the sheath 1211 extending through the self-closing seal 1240. In various embodiments, the laser 1208 and the sheath 1211 can be inserted independently and manually by the user's hand.

As further shown in FIGS. 20A and 20B, the scope 1207 may include a working channel 1210 extending between the distal end 1201 and the proximal end 1203. The working channel 1210 may include the laser 1208 and the sheath 1211 extending through a fluid inlet 1218 defined by the working channel 1210. Although non-limiting, the sheath 1211 may be circular, oval, smile-shaped, D-shaped, etc. In exemplary embodiments, the sheath 1211 may be defined by a thin wall, which is reinforced with a braid or coil such that the ID is maintained even when the sheath 1211 is deflected to allow dust from a bodily mass to pass unimpeded. The laser 1208 can be exposed or extended from the distal end 1201 of the scope 1207 into, e.g., a renal calyx, to fragment/dust the bodily mass, such as one or more renal stones, upon impact. The sheath 1211 may also be extended from the distal end 1201 of the scope 1207 with the laser 1208, wherein an internal channel 1225 of the sheath 1211 is used to remove the fragmented bodily mass. In this embodiment, the internal channel 1225 may correspond to a first lumen, while the fluid inlet 1218 may correspond to a second lumen. The second lumen may be defined by an outer surface 1227 of a wall 1229 of the sheath 1211 and the inner wall(s) of the working channel 1210. The laser 1208 may be positioned within the second lumen, as shown, or may be located within the internal channel 1225 of the sheath 1211.

In various embodiments, the laser 1208 and/or the sheath 1211 can move axially relative to the scope 1207 by advancing or retracting the laser 1208 and the sheath 1211 from the scope 1207 manually or by using the deployment device 1228. When the laser 1208 and the sheath 1211 are retracted into the working channel 1210, the working channel 1210 at the distal end 1201 of the scope 1207 may function as a suction chamber.

As further shown in FIG. 20B, in some embodiments, the scope 1207 may include a feedback device 1216 (e.g., visualization device) positioned within a feedback channel 1222. In some embodiments, the scope 1207 may further include a sensor 1255, such as a pressure sensor or a guide wire sensor operable to control inlet and outlet flow via an automated fluid management system (FMS), e.g., to avoid over and under pressurizing the kidney. As shown, the sensor 1255 may exit a side port 1258 of the scope 1207.

In some embodiments, flow through the inlet and outlet channels (e.g., first and second lumens) can be switched. In some embodiments, the sheath 1211 is used to blow out clogged dust. In other embodiments, the sheath 1211 may be removed or replaced to clean out clogged dust. In other embodiments, the sheath 1211 is the sheath of a retrieval device, such as retrieval basket. The basket can be used to move the stone from the lower pole to the upper pole, for ease of access. In yet other embodiments, the internal components of the retrieval device and handle can be removed, leaving the sheath to be used for suctioning out dust.

Figure 21:
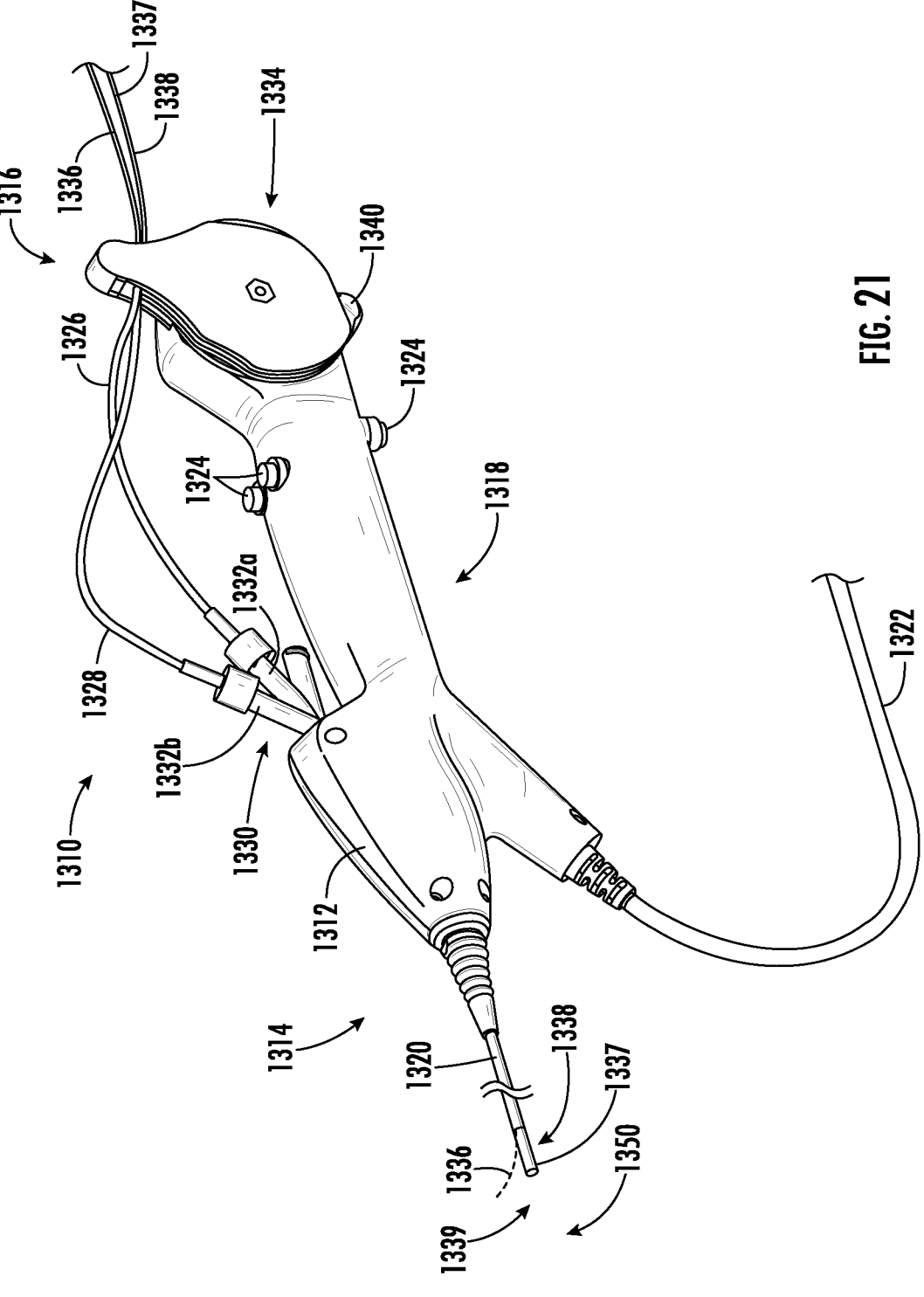
FIG. 21 is a perspective view of an example medical device according to embodiments of the present disclosure.

FIG. 21 is a perspective view of an example medical device 1310. The medical device 1310 may be a deployment device, such as the deployment device 1228 used with the device 1200, described above. The medical device 1310 may include a handle 1312 having a distal end 1314, a proximal end 1316 and a medial region 1318 positioned between the distal end 1314 and the proximal end 1316. It is noted that the terms "proximal" and "distal", as used herein, are intended to refer to a direction toward (proximal) and away from (distal) a user of the device (e.g., physician). Further, the medical device 1310 may include an elongate shaft 1320 extending distally from the handle 1312. In general, the elongate shaft 1320 may take the form of a polymer or metal tube. In some embodiments, the elongate shaft 1320 may be constructed with a reinforcing braid, liner, web, weave, etc.

The elongate shaft 1320 may include a lumen defining a working channel extending through the shaft 1320 from a distal end region of the shaft 1320 to an access port 1330 (e.g., Y-connector) that may be engaged with the handle 1312 or another portion of the medical device 1310. Although the elongate shaft 1320 is described as having a single working channel in FIG. 21, it can be appreciated that in other embodiments, the medical device 1310 may include multiple working channels, as desired.

Further, the handle 1312 may include a deflection knob 1340 or other actuator, which may be used to control movement (e.g., deflection) of the distal tip of the shaft 1320 during operation. For example, the deflection knob 1340 may control up and down movement or deflection of the distal tip of the shaft 1320. In some instances, the deflection knob 1340 may be a self-locking or friction lock type knob which maintains the knob (and the elongate shaft 1320) at its deflected position after being released. The handle 1312 may also include one or a plurality of buttons 1324, which may be used to activate suction or deliver fluid such as air, saline and/or water, etc. through a lumen of the medical device 1310 or perform other functions as desired. These are just examples. Other variations and/or features for medical device 1310 are contemplated.

In some embodiments, a cable 1322 extends from the handle 1312 and is configured for attachment to an electronic device (not pictured) such as e.g. a computer system, a console, a microcontroller, etc. for providing power, analyzing endoscopic data, controlling the endoscopic intervention, or performing other functions. In some embodiments, the electronic device to which the cable 1322 is connected may have functionality for recognizing and exchanging data with other endoscopic accessories.

As discussed above, FIG. 21 illustrates that the handle 1312 of the endoscope may be utilized in conjunction with additional medical devices during a medical procedure. For example, the medical device 1310 may be a ureteroscope (e.g., flexible ureteroscope) utilized in the pulverization and removal of renal stones (e.g., kidney stones). Accordingly, in some examples, the handle 1312 may be utilized in conjunction with a laser fiber 1336 utilized to break up the renal stone and a retrieval device (e.g., retrieval basket) utilized to remove the renal stone pieces. Further, the handle 1312 (and various components thereof) may be utilized to not only manipulate the elongate shaft 1320, but may also be utilized to manipulate a laser fiber 1336 and/or a retrieval device 1338 which may extend though both portions of the handle 1312 and the shaft 1320. While the following disclosure may generally describe the medical device 1310 as being used with a laser fiber 1336 and/or a retrieval device 1338, it can be appreciated that the medical device 1310 (and components thereof) may be used with any elongated medical devices including sheaths, tubular members, guidewires, lasers, or the like.

FIG. 21 further illustrates that the laser fiber 1336 may pass through the first hub 1332a of the access port 1330, continue through the distal end 1314 of the handle 1312 and pass into the working channel of the elongate shaft 1320. After passing through the length of the working channel of the elongate shaft 1320, the laser fiber 1336 may exit the distal end of the elongate shaft 1320 (not shown in FIG. 21).

FIG. 21 illustrates a retrieval device 1338 entering a shaft advancement device 1334 which is coupled to the proximal end region 1316 of the handle 1312. The retrieval device 1338 may include a tubular shaft 1337 having a lumen extending from its distal end to its proximal end. After passing through the shaft advancement device 1334, the retrieval device 1338 may enter the lumen of a first connection tube 1326 (it is noted that the proximal end of the first connection tube 1326 may be fixedly attached to the shaft advancement device 1334). The retrieval device 1338 may continue passing through the lumen of the first connection tube 1326 into a first hub 1332a of an access port 1330. While FIG. 21 illustrates the access port 1330 including three hubs, it can be appreciated that the access port 1330 may include more of less than three hubs. For example, the access port 1330 may include 1, 2, 3, 4, 5, 6 or more hubs.

Additionally, the access port 1330 may include a variety of different geometric shapes that may include one or more hubs configured to connect to one or more connection tubes. Further, in some examples, the access port 1330 may be eliminated from the handle 1312. In these examples, the handle housing, itself, may include one or more hubs extending directly from the outer surface of the handle housing. These hubs may be utilized to attach directly to one or more connection tubes.

FIG. 21 further illustrates that the retrieval device 1338 may pass through the first hub 1332a of the access port 1330, continue through the distal end 1314 of the handle 1312 and pass into the working channel of the elongate shaft 1320, or an additional working channel of the elongate shaft 1320. After passing through the length of the working channel of the elongate shaft 1320, the retrieval device 1338 may exit the distal end of the elongate shaft 1320, as shown in FIG. 21.

FIG. 21 further illustrates that, in some examples, the retrieval device 1338 may include an end effector, such as a retrieval basket 1350, for manipulation and/or grasping particulates, such as renal stone fragments. The retrieval device 1338 may include a retrieval wire 1339 extending within the lumen of the tubular shaft 1337 of the retrieval device 1338 for manipulating the end effector, such as the retrieval basket 1350. For example, FIG. 21 illustrates that, in some examples, a retrieval wire 1339 may enter the lumen of the tubular shaft 1337 of the retrieval device 1338 at its proximal end, pass through the lumen of the tubular shaft 1337 of the retrieval device 1338 (and consequently, through the first connection tube 1326, the first hub 1332a, the distal end 1314 of the handle 1312 and through the working channel of the elongate shaft 1320) before exiting the distal end of the tubular shaft 1337 of the retrieval device 1338.

While FIG. 21 illustrates the retrieval wire 1339 as including a retrieval basket 1350, it can be appreciated that the retrieval wire 1339 may include a variety of different end effectors that are utilized in conjunction with the retrieval device 1338. For example, the retrieval wire 1339 may include a retrieval net, forceps, an immobilization device, a stone sweeping device, or other similar medical devices.

It can be appreciated that, in some examples the retrieval basket 1350 may shift from a first, unexpanded configuration to a second, expanded configuration by longitudinally actuating the retrieval wire 1339 relative to the tubular member of the retrieval device 1338. During use, the retrieval basket 1350 may be utilized to capture a renal stone, or fragments thereof, when in the expanded configuration. After being captured in the retrieval basket 1350, a clinician may remove the renal stone and/or fragments from the body by retracting the retrieval basket 1350 proximally toward the distal end of the tubular shaft 1337 of the retrieval device 1338 to close the retrieval basket 1350 around the renal stone and/or fragment. It can be appreciated that the renal stone and/or fragment may remain trapped in the retrieval basket 1350 while remaining outside the lumen of the tubular member of the retrieval device 1338. To remove the renal stone and/or fragment from the body, the clinician may withdraw the retrieval device 1338 proximally through the working channel of the elongate shaft 1320 of the medical device 1310 from the patient's body.

Like that described with respect to the retrieval device 1338, FIG. 21 illustrates a laser fiber 1336 entering the shaft advancement device 1334 which is coupled to the proximal end region 1316 of the handle 1312. After passing through the shaft advancement device 1334, the laser fiber 1336 may enter the lumen of a second connection tube 1328 (it is noted that the proximal end of the second connection tube 1328 may be fixedly attached to the shaft advancement device 1334). The laser fiber 1336 may continue passing through the lumen of the second connection tube 1328 into a second hub 1332b of the access port 1330. It can be appreciated that FIG. 21 shows the retrieval device 1338 extending out of the distal end of the elongate shaft 1320 while the distal end of the laser fiber 1336 is shown in dashed lines simply for illustrative purposes. Therefore, it can be appreciated that during a medical procedure, only one or the other of the laser fiber 1336 or the retrieval device 1338 (including the retrieval wire 1339 positioned within the lumen of the tubular shaft 1337 of the retrieval device 1338) may occupy the working channel of the elongate shaft 1320 while the other of the laser fiber 1336 and the retrieval device 1338 may be positioned proximal of the access port 1330 within either of the first connection tube 1326 or the second connection tube 1328. In other instances, the laser fiber 1336 may occupy a first working lumen of the elongate shaft 1320 while the retrieval device 1338, including the tubular shaft 1337 of the retrieval device 1338 and retrieval wire 1339 extending therethrough, occupies the second working lumen of the elongate shaft 1320. It can be appreciated that, in some examples, each of the first connection tube 1326 and the second connection tube 1328 may be transparent or translucent, thereby permitting a clinician to visualize the distal end of the laser fiber 1336 or the distal end of the retrieval device 1338 located therein when withdrawn from the working channel of the elongate shaft 1320 to permit the other device to occupy the working channel of the elongate shaft 1320. It may be desirable for a clinician to be able to visually confirm that the distal end of the retrieval device 1338 or the distal end of the laser fiber 1336 is located in either the first connection tube 1326 or the second connection tube 1328, respectively, when the other of the retrieval device 1338 and the laser fiber 1336 is advanced distally into the working channel of the elongate shaft 1320.

For example, a medical procedure to remove a renal stone may include manipulation of the shaft advancement device 1334 (described in greater detail below) to advance the laser fiber 1336 into the second connection tube 1328 such that the laser fiber 1336 is positioned just proximal of the second hub 1332*b* of the access port 1330. As discussed above, the distal end of the laser fiber 1336 may be visible within the transparent or translucent connection tube 1328 when positioned proximal of the second hub 1332*b*. Next, the shaft advancement device 1334 may be utilized to advance the retrieval device 1338 (including the tubular shaft 1337 of the retrieval device 1338 and the retrieval wire 1339 disposed therein) into the first connection tube 1326 such that the retrieval device 1338 is positioned just proximal of the first hub 1332*a* of the access port 1330. As discussed above, the distal end 1314 of the retrieval device 1338 may be visible within the transparent or translucent connection tube 1326 when positioned proximal of the first hub 1332*a*. In this configuration, each of the retrieval device 1338 and the laser fiber 1336 may be referred to as being "parked" in its respective connection tube 1326/1328 in order to permit the other to be advanced into the working channel of the elongate shaft 1320.

An example next step in the procedure may include a physician manipulating the shaft advancement device 1334 to advance the laser fiber 1336 through the working channel of the elongate shaft 1320 to the target site, whereby the laser fiber 1336 may be utilized to pulverize the renal stone. Next, the physician may utilize the advancement device 1334 to retract the laser fiber 1336 proximally until the distal end of the laser fiber 1336 is positioned proximal of the second hub 1332*b* and back into the second connection tube 1328. It can be appreciated that when the distal tip of the laser fiber 1336 is seen through the transparent or translucent connection tube 1328, the laser fiber 1336 is cleared from the working channel of the elongate shaft 1320. It can be appreciated that retracting the laser fiber 1336 back into the second connection tube 1328 may open up the working channel of the elongate shaft 1320 to subsequently permit the retrieval device 1338 to be advanced distally therethrough. Accordingly, a next step in the procedure may include a physician manipulating the shaft advancement device 1334 to advance the retrieval device 1338 distally through the working channel of the elongate shaft 1320 to the target site, whereby the retrieval basket 1350 may be deployed distal of the distal end of the elongate shaft 1320 of the medical device 1310 to capture the kidney stone and/or fragments.

As discussed above, the renal stone and/or fragments may remain trapped in the retrieval basket 1350 while the clinician withdraws the retrieval device 1338 and the elongate shaft 1320 of the medical device 1310 from the patient's body. The medical device 1310 may thereafter be reinserted into the body to capture additional renal stones and/or fragments, if desired.

FIGS. 22-25B and the corresponding discussion below will describe the components and function of the shaft advancement device 1334.

Figure 22:
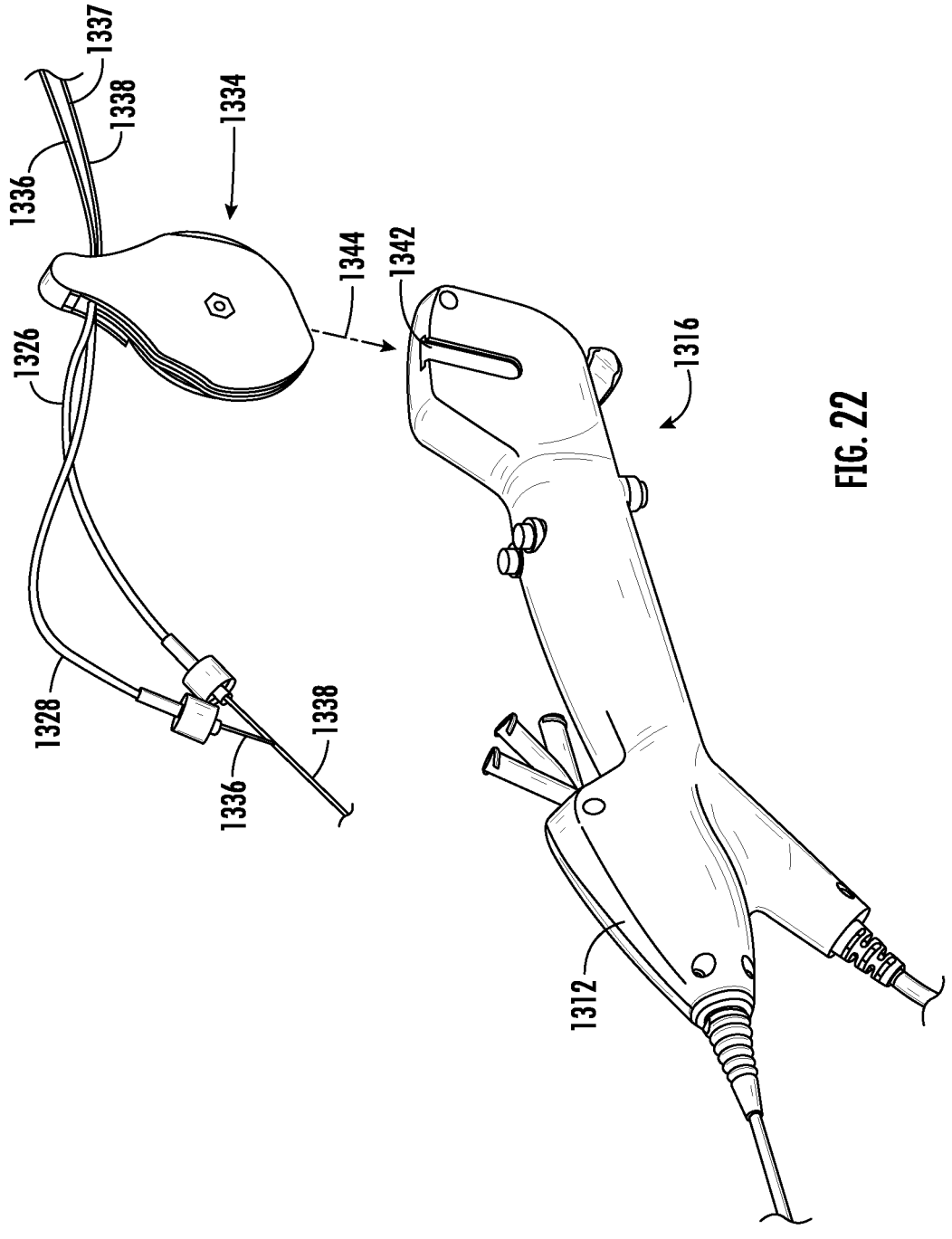
FIG. 22 is another perspective view of the example medical device shown in FIG. 21 according to embodiments of the present disclosure.

FIG. 22 illustrates that the shaft advancement device 1334 may be removably coupled to the proximal end region 1316 of the handle 1312. In other instances, the shaft advancement device 1334 may be coupled to the proximal end region 1316 of the handle 1312 in another manner. As described in FIG. 21, FIG. 22 illustrates the retrieval device

1338 and the laser fiber 1336 passing through the shaft advancement device 1334 and through the first connection tube 1326 and the second connection tube 1328, respectively. While the shaft advancement device 1334 has been described as being removably coupled to the handle 1312, it is contemplated that, in some embodiments, the shaft advancement device 1334 may be integrated with and/or fixedly attached to the handle 1312 such that its removal from the handle 1312 is not intended.

As shown in FIG. 22, the shaft advancement device 1334 may be coupled to the handle 1312 via insertion of an engagement feature of the shaft advancement device 1334 into a slot 1342 located in the proximal end region 1316 of the handle 1312. As will be shown in FIG. 23, the slot 1342 may be designed to accept an axle (shown in FIG. 23) located on a housing component of the shaft advancement device 1334. The insertion of the axle into the slot 1342 of the handle 1312 is depicted with the arrow 1344 of FIG. 22. In other embodiments, the shaft advancement device 1334 may include a different engagement feature (e.g., post, pin, fastener, etc.) configured to engage with the slot 1342 of other engagement feature of the handle 1312. It can be appreciated that the shaft advancement device 1334 may be packaged as a separate device that is optionally coupled to the handle 1312 when desired. For example, a physician may opt to attach the shaft advancement device 1334 prior to procedures involving the manipulation of the handle 1312 and additional medical devices such as the laser fiber 1336 and the retrieval device 1338. It can be appreciated that the physician may remove the shaft advancement device 1334 from the handle 1312 when desired.

Figure 23:
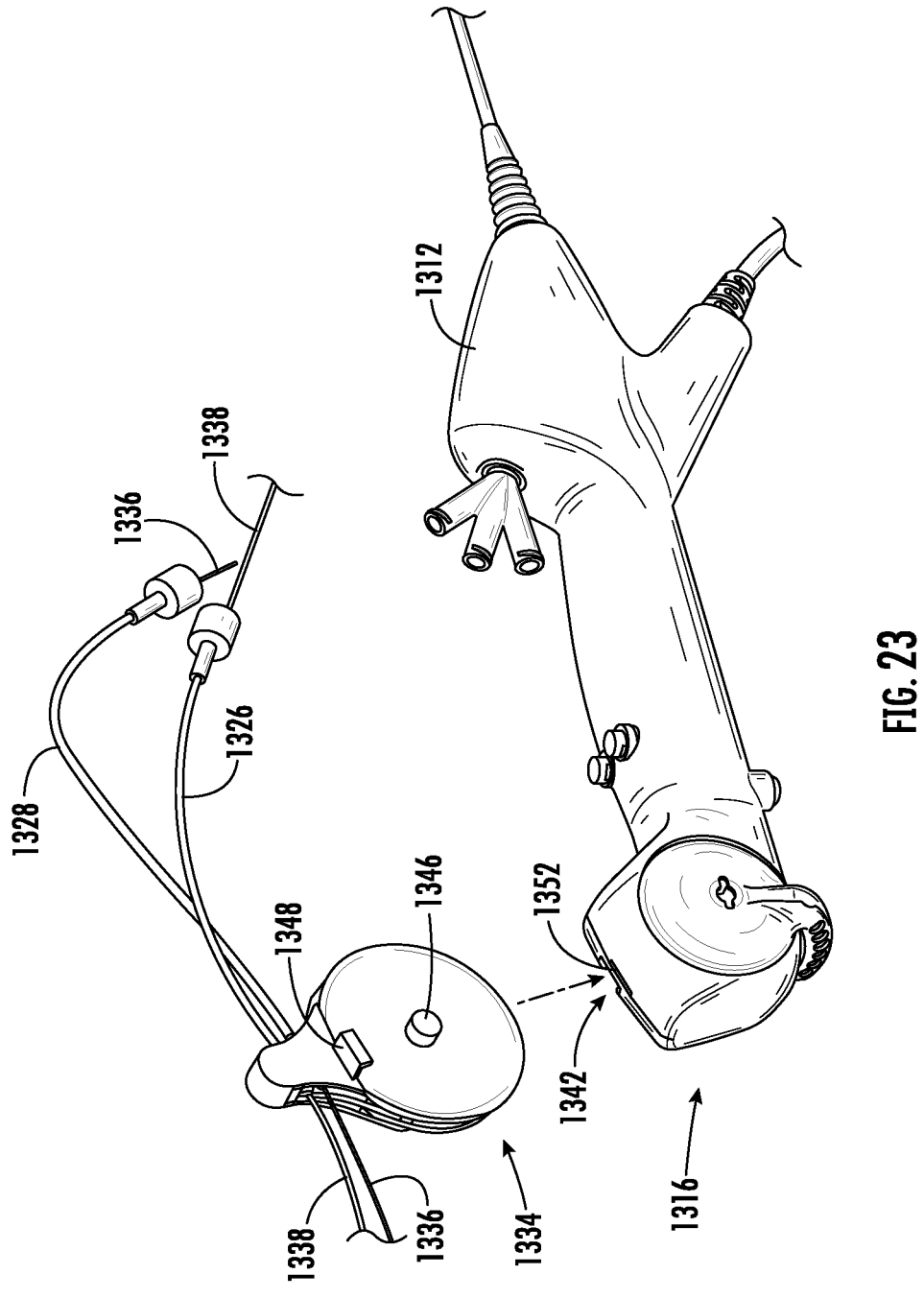
FIG. 23 is another perspective view of the example medical device shown in FIG. 21 according to embodiments of the present disclosure.

As discussed above, FIG. 23 illustrates the insertion of the axle 1346 of the shaft advancement device 1334 into a slot 1342 of the handle 1312. Additionally, FIG. 23 illustrates that the shaft advancement device 34 may further include a post (e.g., clip) 1348 which is designed to be inserted into a recess 1352 located along the distal end region 1316 of the handle 1312. It can be appreciated that the recess 1352 may be positioned adjacent to the upper region of the slot 1342.

It can be further appreciated that the engagement of the axle 1346 within the slot 1342, in combination with the insertion of the flat portion of the post or clip 1348 into the recess 1352, may limit rotation of the shaft advancement device 1334 when coupled with the handle 1312 in addition to providing a sufficient retention force such that the shaft advancement device 1334 will not inadvertently separate from the handle 1132 during a medical procedure. For example, the dimensions of the axle 1346 and the post or clip 1348 may be designed such that they provide a press fit or interlocking fit within the slot 1342 and the recess 1352, respectively.

Figure 24:
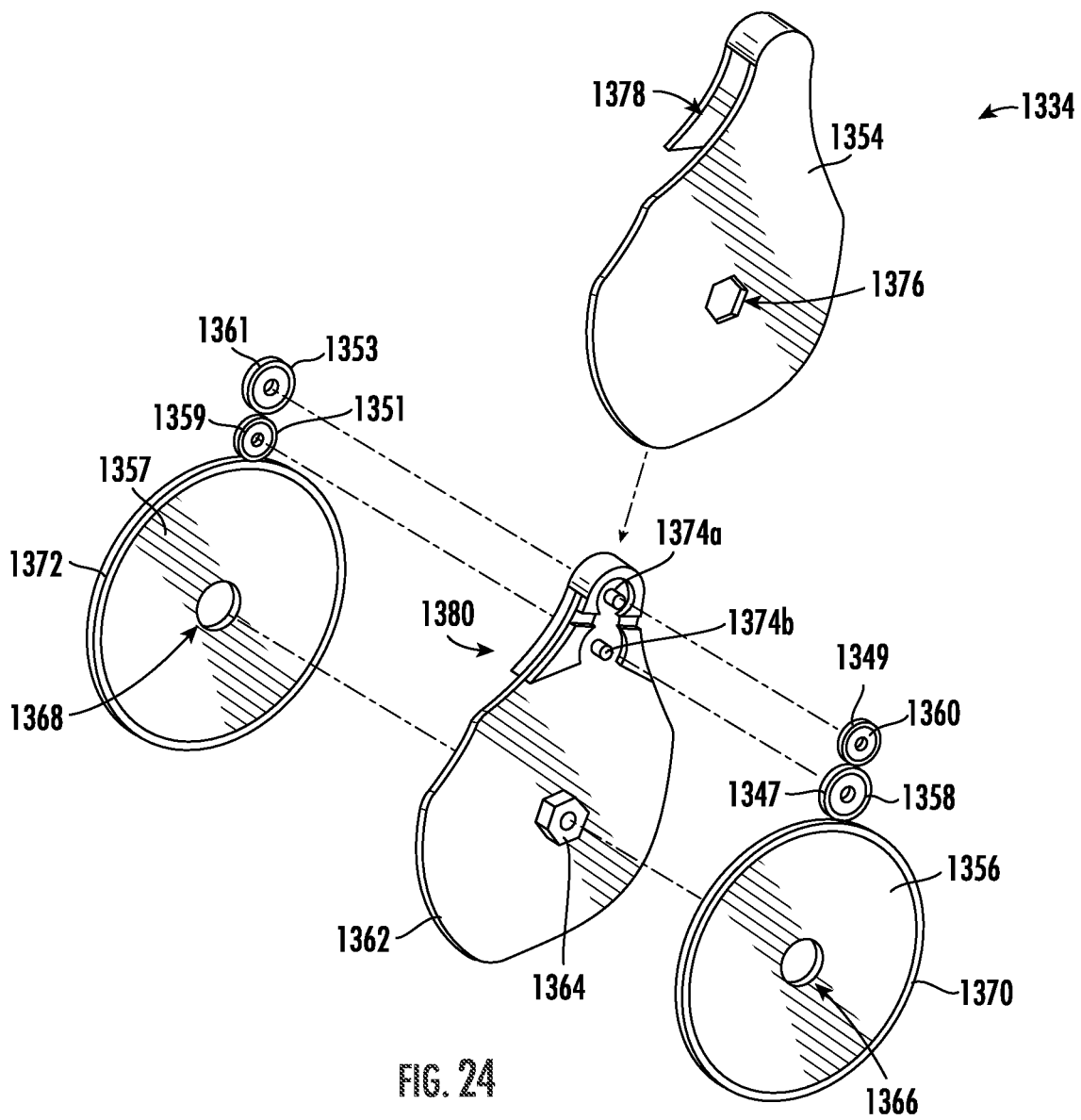
FIG. 24 is an exploded view of the components of a shaft advancement mechanism of the medical device shown in FIG. 23 according to embodiments of the present disclosure.

FIG. 24 illustrates an exploded view of the shaft advancement device 1334 described above. For clarity, the first connection shaft 1326, the second connection shaft 1328, the laser fiber 1336, and the retrieval device 1338 have been omitted from FIG. 24.

FIG. 24 illustrates that shaft advancement device 1334 may include a housing, including an inner housing 1362 (e.g., first housing member) which may be positioned (e.g., "sandwiched") between a first thumbwheel 1356 and a second thumbwheel 1357, and an outer housing 1354 (e.g., a second housing member). The first thumbwheel 1356 may be coupled to the inner housing 1362 via the extension of an axle 1364 of the inner housing 1362 through an aperture 1366 of the first thumbwheel 1356. FIG. 24 illustrates that the axle 1364 of the inner housing 1362 may be generally located in a central region of the inner housing 1362.

Further, FIG. 24 illustrates that the axle 1364 may be generally shaped as a hexagon. However, while FIG. 24 shows the axle 1364 including a hexagon shape in FIG. 24, it can be appreciated that the axle 1364 may include a variety of shapes. For example, the axle 1364 could include a cylindrical, triangular, polygonal, square, or other similar shapes.

Similarly, the second thumbwheel 1357 may be coupled to the inner housing 1362 via the extension of the axle 1346 (not visible in FIG. 24, but shown in FIG. 23) of the inner housing 1362 through an aperture 1368 of the second thumbwheel 1357. FIG. 24 illustrates that the axle 1346 of the inner housing 1362 may be generally located in a central region of the inner housing 1362. It can be appreciated that the axle 1346 may be axially aligned with the axle 1364. Additionally, FIG. 24 illustrates that the axle 1346 may be generally shaped as a cylinder. However, while FIG. 24 shows the axle 1346 including a cylindrical shape in FIG. 24, it can be appreciated that the axle 1346 may include a variety of shapes. For example, the axle 1346 could include a hexagon, triangular, polygonal, square, or other similar shapes. Additionally, it can be appreciated that each of the first thumbwheel 1356 and the second thumbwheel 1357 may be press fit onto the axle 1364 and the axle 1346, respectively while allowing rotation of the first and second thumbwheels 1356/1357 relative thereto.

FIG. 24 further illustrates that each of the first thumbwheel 1356 and the second thumbwheel 1357 may include a band of material which extends circumferentially around the perimeter of each of the first thumbwheel 1356 and the second thumbwheel 1357. For example, the first thumbwheel 1356 may include a band 1370 of material that extends circumferentially around the perimeter of the first thumbwheel 1356. Similarly, the second thumbwheel 1357 may include a band 1372 of material that extends circumferentially around the perimeter of the second thumbwheel 1357. The material that is used to construct the band of material 1370 and the band of material 1372 may be designed too generally include materials which provide grip when a user is manipulating the first thumbwheel 1356 and/or the second thumbwheel 1357. For example, the band of material 1370 and the band of material 1372 may include rubber, silicone, nitrile butadiene rubber, thermoplastic elastomers, neoprene, or similar materials.

Additionally, in some examples, the band of material band 1370 and the band of material 1372 may include an elastic material. Utilization of an elastic material to construct the band of material 1370 and the band of material 1372 may be advantageous as an elastic material may be resistant to being removed from the first thumbwheel 1356 and/or the second thumbwheel 1357. In other words, an elastic material may provide a compressing force onto the outer circumferential surface of the first thumbwheel 1356 and/or the second thumbwheel 1357. Further, band of material 1370 and the band of material 1372 may include a roughened or textured surface that is suitable to be in contact with both other wheels and the thumb of a user.

When assembled, it can be appreciated that the first thumbwheel 1356 and/or the second thumbwheel 1357 may be rotated around the axles 1364 and 1346, respectively, in ether a clockwise or counterclockwise direction. Further, as will be described in greater detail below, a physician may use their thumb (or another finger) of their hand grasping the handle 1312 of the medical device 1310 to manually rotate the first thumbwheel 1356 and/or the second thumbwheel 1357. It can be appreciated that each of the first thumbwheel 1356 and/or the second thumbwheel 1357 may be rotated in either direction (e.g., each of the first thumbwheel 1356 and/or the second thumbwheel 1357 may be rotated in a clockwise direction or a counterclockwise direction).

FIG. 24 further illustrates that the shaft advancement device 1334 may include a first drive wheel 1358. The first drive wheel 1358 may be coupled to the inner housing 1362 via a pin 1374_b_, which extends away from the surface of the inner housing 1362. It can be appreciated that the first drive wheel 1358 may rotate in a clockwise direction or a counterclockwise direction around the axis of the pin 1374_b_. Additionally, FIG. 24 illustrates that the first drive wheel 1358 may include a band of material 1347 extending circumferentially around its perimeter. The circumferential surface of the first drive wheel 1358 may be in direct contact with the circumferential surface of the first thumbwheel 1356. The band of material 1347 may be similar in form and function as the band of material 1370 described above. Additionally, FIG. 24 illustrates that the first drive wheel 1358 may be in contact with the first thumbwheel 1356 (e.g., the band of material 1370 of the first thumbwheel 1356 may directly contact the band of material 1347 of the first drive wheel 1358).

FIG. 24 further illustrates that the shaft advancement device 1334 may include a first roller wheel 1360. The first roller wheel 1360 may be coupled to the inner housing 1362 via a pin 1374_a_, which extends away from the surface of the inner housing 1362. It can be appreciated that the first roller wheel 1360 may rotate in a clockwise direction or a counterclockwise direction around the axis of the pin 1374_a_. Additionally, FIG. 24 illustrates that the first roller wheel 1360 may include a band of material 1349 extending circumferentially around its perimeter. The band of material 1349 may be similar in form and function as the band of material 1370 described above. The circumferential surface of the first drive wheel 1358 may be placed adjacent to the circumferential surface of the first roller wheel 1360. For example, FIG. 24 illustrates that the first roller wheel 1360 may be in contact with the first drive wheel 1358 (e.g., the band of material 1347 of the first drive wheel 1358 may directly contact the band of material 1349 of the first roller wheel 1358), or a small gap may remain therebetween for placement of the tubular shaft 1337 of the retrieval device 1338 therebetween.

As will be described in greater detail below, because the first thumbwheel 1356 directly contacts the first drive wheel 1358, rotation of the first thumbwheel 1356 will cause rotation of the first drive wheel 1358 in a direction that is opposite to the rotation of the first thumbwheel 1356. For example, clockwise rotation (as viewed from the outer surface of the thumbwheel 1356) of the first thumbwheel 1356 will cause a counterclockwise rotation of the first drive wheel 1358. Similarly, because the first drive wheel 1358 directly contacts the first roller wheel 1360, rotation of the first drive wheel 1358 will cause rotation of the first roller wheel 1360 in a direction that is opposite to the rotation of the first drive wheel 1358. For example, counterclockwise rotation of the first drive wheel 1358 will cause a clockwise rotation of the first roller wheel 1360. It can further be appreciated that the rotation of the first thumbwheel 1356 results in the first roller wheel 1360 being rotated in the same direction as the first thumbwheel 1356 (while the first drive wheel 1358 is rotated in an opposite direction to both the first thumbwheel 1356 and the first roller wheel 1360).

The first thumbwheel 1356 may have a diameter greater than the diameter of the first drive wheel 1358 to provide a mechanical advantage. For example, the diameter of the first thumbwheel 1356 may be two times or more, three times or more, or four times or more of the diameter of the first drive wheel 1358. Thus, one full revolution of the first thumbwheel 1356 may result in greater than one full revolution of the first drive wheel 1358. In some instances, the first thumbwheel 1356 may be sized relative to the first drive wheel 1358 in a 2:1 ratio, a 3:1 ratio, a 4:1 ratio, or a 5:1 ratio, for example.

FIG. 24 further illustrates that the shaft advancement device 1334 may include a second drive wheel 1359. The second drive wheel 1359 may be coupled to the inner housing 1362 via a pin (not visible in FIG. 24), which extends away from the surface of the inner housing 1362. It can be appreciated that the second drive wheel 1359 may rotate in a clockwise direction or a counterclockwise direction. Additionally, FIG. 24 illustrates that the second drive wheel 1359 may include a band of material 1351 extending circumferentially around its perimeter. The circumferential surface of the second drive wheel 1359 may be in direct contact with the circumferential surface of the second thumbwheel 1357. The band of material 1351 may be similar in form and function as the band of material 1372 described above. Additionally, FIG. 24 illustrates that the second drive wheel 1359 may be in contact with the second thumbwheel 1357 (e.g., the band of material 1372 of the second thumbwheel 1357 may directly contact the band of material 1351 of the second drive wheel 1359).

FIG. 24 further illustrates that the shaft advancement device 1334 may include a second roller wheel 1361. The second roller wheel 1361 may be coupled to the inner housing 1362 via a pin (not visible in FIG. 24), which extends away from the surface of the inner housing 1362. It can be appreciated that the second roller wheel 1361 may rotate in clockwise direction or a counterclockwise direction. Additionally, FIG. 24 illustrates that the second roller wheel 1361 may include a band of material 1353 extending circumferentially around its perimeter. The band of material 1353 may be similar in form and function as the band of material 1372 described above. The circumferential surface of the second drive wheel 1359 may be placed adjacent to the circumferential surface of the second roller wheel 1361. For example, FIG. 24 illustrates that the second roller wheel 1361 may be in contact with the second drive wheel 1359 (e.g., the band of material 1351 of the second drive wheel 1359 may directly contact the band of material 1353 of the second roller wheel 1361), or a small gap may remain therebetween for placement of the laser fiber 1336 therebetween.

As will be described in greater detail below, because the second thumbwheel 1357 directly contacts the second drive wheel 1359, rotation of the second thumbwheel 1357 will cause rotation of the second drive wheel 1359 in a direction that is opposite to the rotation of the second thumbwheel 1357. For example, counterclockwise rotation (as view from the outer surface of the second thumbwheel 1357) of the second thumbwheel 1357 will cause a clockwise rotation of the second drive wheel 1359. Similarly, because the second drive wheel 1359 directly contacts the second roller wheel 1361, rotation of the second drive wheel 1359 will cause rotation of the second roller wheel 1361 in a direction that is opposite to the rotation of the second drive wheel 1359. For example, clockwise rotation of the second drive wheel 1359 will cause a counterclockwise rotation of the second roller wheel 1361. It can be further appreciated that the rotation of the second thumbwheel 1357 results in the second roller wheel 1361 being rotated in the same direction as the second thumbwheel 1357 (while the second drive wheel 1359 is rotated in an opposite direction to both the second thumbwheel 1357 and the second roller wheel 1361).

The second thumbwheel 1357 may have a diameter greater than the diameter of the second drive wheel 1359 to provide a mechanical advantage. For example, the diameter of the second thumbwheel 1357 may be two times or more, three times or more, or four times or more of the diameter of the second drive wheel 1359. Thus, one full revolution of the second thumbwheel 1357 may result in greater than one full revolution of the second drive wheel 1359. In some instances, the second thumbwheel 1357 may be sized relative to the second drive wheel 1359 in a 2:1 ratio, a 3:1 ratio, a 4:1 ratio, or a 5:1 ratio, for example.

It can be appreciated one or more of the "wheels" described herein (including all the wheels described with respect to FIG. 24) do not necessarily have to directly contact one another to rotate one another. Rather, in some examples, one or more of the wheels may be connected via belts or chains, etc. to pulleys or gears, etc. attached to the wheels. For example, independent wheels may each include a gear whereby each gear of the two wheels are coupled to each other via a drive belt or drive chain. It can be appreciated that the rotation of one wheel will rotate the other wheel via the drive belt or drive chain connection. Further, gear ratios may be employed to tailor the speed/force of the drive wheels.

FIG. 24 further illustrates that the housing of the shaft advancement device 1334 may include an outer housing 1354. The outer housing 1354 may be designed such that it covers a portion of the lateral (outer facing) surface of the first thumbwheel 1356 without covering a corresponding lateral (outer facing) surface of the second thumbwheel 1357. However, in other instances, the outer housing 1354 may be designed to cover a lateral (outer facing) surface of the second thumbwheel 1357, if desired. Further, FIG. 24 illustrates the outer housing 1354 may include an aperture 1376 through which the axle 1364 may extend (e.g., the outer housing 1354 may be attached to the inner housing 1362 via engagement of the axle 1364 through the aperture 1376).

Additionally, the outer housing 1354 may be positioned over a portion of the inner housing 1362, the first thumbwheel 1356, the first drive wheel 1358, the first roller wheel 1360, the second drive wheel 1359 and the second roller wheel 1361. Referring back to FIGS. 22-23, the outer housing 1354 is shown positioned over a portion of the inner housing 1362, the first thumbwheel 1356, the first drive wheel 1358, the first roller wheel 1360, the second drive wheel 1359 and the second roller wheel 1361. Referring back to FIG. 22, the axle 1364 is shown extending through the aperture 1376 of the outer housing 1354. It can be further appreciated that the outer housing 1354 may include a channel 1378 which is designed to accept the upper head portion 1380 of the inner housing 1362. The upper head portion 1380 of the inner housing 1362 may be defined as that portion of the inner housing 1362 which includes the first drive wheel 1358, the first roller wheel 1360, the second drive wheel 1359 and the second roller wheel 1361. It can be appreciated from FIGS. 22-23, that, when assembled, the outer housing 1354 may cover the first drive wheel 1358, the first roller wheel 1360, the second drive wheel 1359 and the second roller wheel 1361 while permitting a user to access and rotate the first thumbwheel 1356 and the second thumbwheel 1357.

Figure 25A:
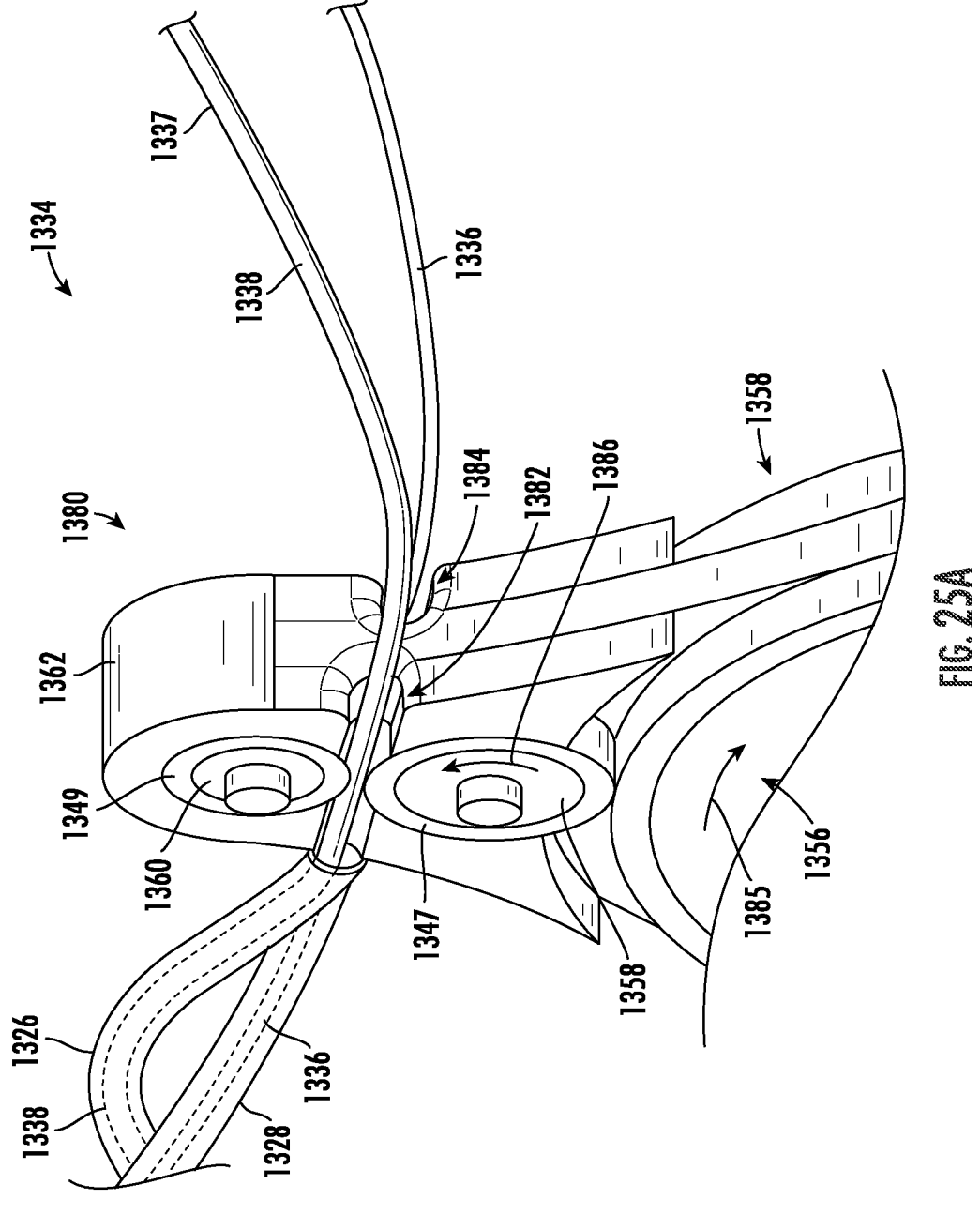
FIG. 25A is a detailed view of the shaft advancement mechanism of the medical device shown in FIG. 21 according to embodiments of the present disclosure.

FIG. 25A illustrates a detailed view of the shaft advancement device 1334 (for clarity, the outer housing 1354 has been omitted from FIG. 25A). In particular, FIG. 25A illustrates the upper head portion 1380 of the inner housing 1362 which includes the first drive wheel 1358, the first roller wheel 1360, the second drive wheel 1359 (not visible in FIG. 25A, but shown in FIG. 25B) and the second roller wheel 1361 (not visible in FIG. 25A, but shown in FIG. 25B). Additionally, FIG. 25A illustrates that first drive wheel 1358 in direct contact with the first thumbwheel 1356.

Additionally, FIG. 25A illustrates the laser fiber 1336 extending through an opening 1384 formed in the inner housing 1362 and the retrieval device 1338 extending through an opening 1382 formed in the inner housing 1362 (it can be appreciated from the above discussion that the retrieval wire 1339 may extend through the tubular shaft 1337 of the retrieval device 1338 but is not visible in FIG. 25A). The tubular shaft 1337 of the retrieval device 1338 may be sandwiched (i.e., pressed) between the first drive wheel 1358 and the first roller wheel 1360 (e.g., between the band of material 1347 of first drive wheel 1358 and the band of material 1349 of the first roller wheel 1360).

The proximal end of the first connection tube 1326 may be fixedly attached to the housing, such as the inner housing 1362. For example, the proximal end of the first connection tube 1326 may be adhesively attached to the inner housing 1362. Other attachment methods are contemplated to fixedly attach the proximal end of the first connection tube 1326 to the housing (e.g., the inner housing 1362). For example, the proximal end of the first connection tube 1326 may be flared while the housing 1362 may include a projection designed to engage and mate with the flared portion of the first connection tube 1326. In other examples, the proximal end of the first connection tube 1326 may be expanded over a barb fitting of the housing 1362. Additionally, FIG. 25A illustrates that after passing between the first drive wheel 1358 and the first roller wheel 1360, the retrieval device 1338, or other elongate shaft of a medical device, may enter the lumen of the first connection tube 1326 (the retrieval device 1338 is depicted within the lumen of the first connection tube 1326 via dashed lines).

FIG. 25A illustrates the mechanism by which the retrieval device 1338 is advanced (or retracted) into and out of the working channel of the elongate shaft 1320 (as described above) via manipulation of the first thumbwheel 1356. As described above, the clockwise rotation (depicted by arrow 1385) of the first thumbwheel 1356 will result in the counterclockwise rotation (depicted by arrow 1386) of the first drive wheel 1358. The counterclockwise rotation of the first drive wheel 1358 will translate the retrieval device 1338 in a distal direction (e.g., it will drive/push the retrieval device 1338 into the lumen of the first connection tube 1326). Additionally, it can be appreciated that the counterclockwise rotation of the first thumbwheel 1356 reverses the rotation of the first drive wheel 1358 and thereby retracts the retrieval device 1338 proximally.

It can be appreciated that the ability of the first drive wheel 1358 to translate the retrieval device 1338 relative to the first connection tube 1326 and the working channel of the elongate shaft 1320 is created via a compressive force imparted onto the retrieval device 1338 as it is sandwiched between the first drive wheel 1358 and the first roller wheel 1360. It can be further appreciated that the first drive wheel 1358 and the first roller wheel 1360 must be spaced apart from one another to permit the first drive wheel 1358 to sufficiently advance the retrieval device 1338 within the first connection tube 1326 (and the working channel of the elongate shaft 1320) without slipping while also making the tactile feedback of the first thumbwheel 1356 comfortable for the user. In some examples, the first drive wheel 1358 and/or the first roller wheel 1360 may be attached to a spring such that the spacing between first drive wheel 1358 and/or the first roller wheel 1360 is adjustable for elongate shafts of medical devices having varying outer diameters.

Figure 25B:
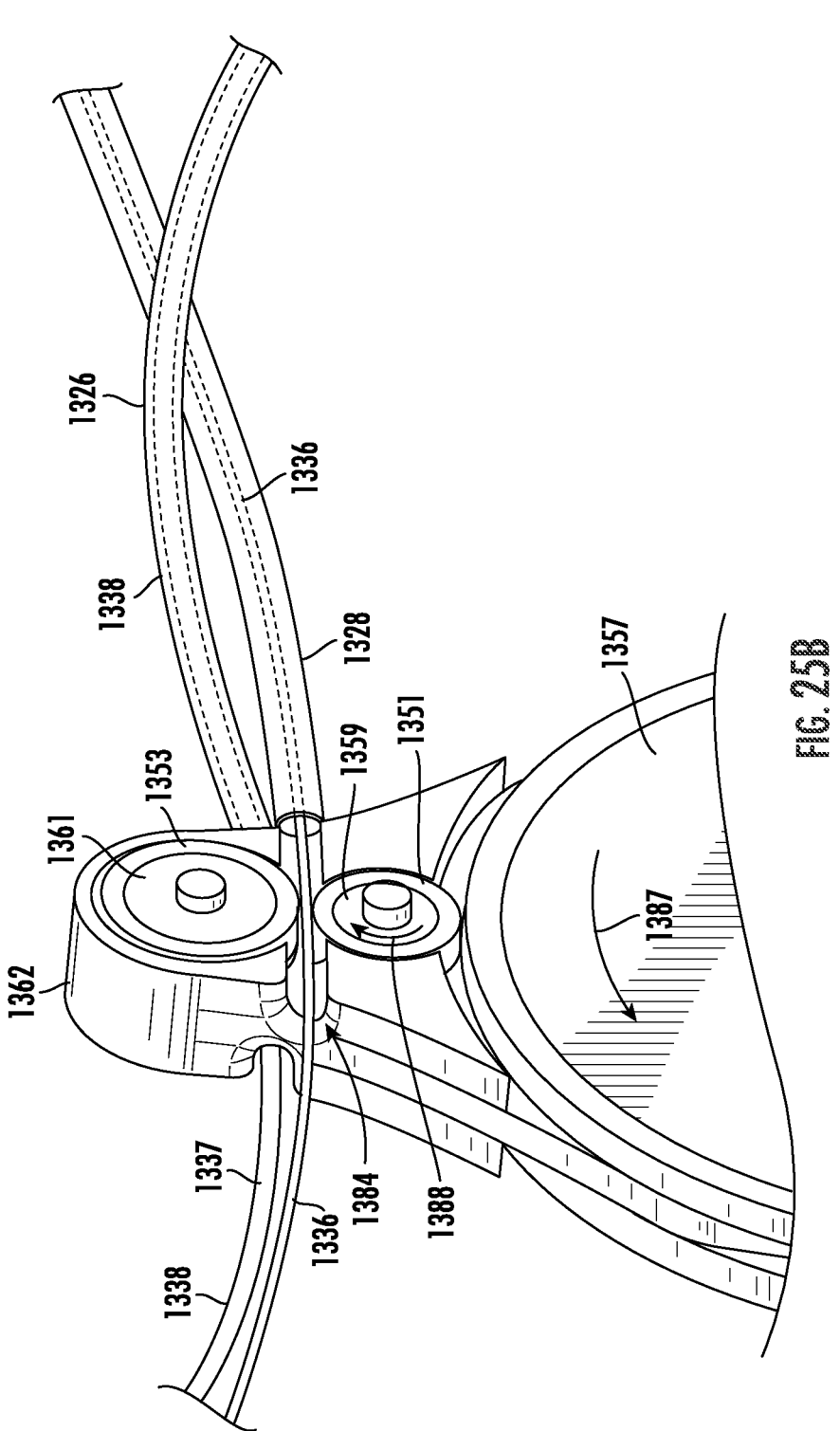
FIG. 25B is another detailed view of the shaft advancement mechanism of the medical device shown in FIG. 21 according to embodiments of the present disclosure.

FIG. 25B illustrates FIG. 25A rotated to show the laser fiber 1336 extending through an opening 1384 formed in the inner housing 1362. Further, FIG. 25B illustrates that the laser fiber 1336 may be sandwiched (i.e., pressed) between the second drive wheel 1359 and the second roller wheel 1361 (e.g., between the band of material 1351 of second drive wheel 1359 and the band of material 1353 of the first roller wheel 1361).

The proximal end of the second connection tube 1328 may be fixedly attached to the housing, such as the inner housing 1362. For example, the proximal end of the second connection tube 1328 may be adhesively attached to the inner housing 1362. Other attachment methods are contemplated to fixedly attach the proximal end of the second connection tube 1328 to the housing (e.g., the inner housing 1362). For example, the proximal end of the second connection tube 1328 may be flared while the housing 1362 may include a projection designed to engage and mate with the flared portion of the second connection tube 1328. In other examples, the proximal end of the second connection tube 1328 may be expanded over a barb fitting of the housing 1362. Additionally, FIG. 25B illustrates that after passing between the second drive wheel 1359 and the second roller wheel 1361, the laser fiber 1336, or other elongate shaft of a medical device, may enter the lumen of the second connection tube 1328 (the laser fiber 1336 is depicted within the lumen of the second connection tube 1328 via dashed lines).

FIG. 25B illustrates the mechanism by which the laser fiber 1336 is advanced (or retracted) into and out of the working channel of the elongate shaft 1320 (as described above) via manipulation of the second thumbwheel 1357. As described above, the counterclockwise rotation (depicted by arrow 1387) of the second thumbwheel 1357 will result in the clockwise rotation (depicted by arrow 1388) of the second drive wheel 1359. The clockwise rotation of the second drive wheel 1359 will translate the laser fiber 1336 in a distal direction (e.g., it will drive/push the laser fiber 1336 into the lumen of the second connection tube 1328). Additionally, it can be appreciated that the clockwise rotation of the second thumbwheel 1357 reverses the rotation of the second drive wheel 1359 and thereby retracts the laser fiber 1336 proximally.

It can be appreciated that the ability of the second drive wheel 1359 to translate the laser fiber 1336 relative to the second connection tube 1328 and the working channel of the elongate shaft 1320 is created via a compressive force imparted onto the laser fiber 1336 as it is sandwiched between the second drive wheel 1359 and the second roller wheel 1361. It can be further appreciated that the second drive wheel 1359 and the second roller wheel 1361 must be spaced apart from one another to permit the second drive wheel 1359 to sufficient advance the laser fiber 36 within the second connection tube 28 (and the working channel of the elongate shaft 20) without slipping while also making the tactile feedback of the second thumbwheel 57 comfortable for the physician. In some examples, the second drive wheel 59 and/or the second roller wheel 1361 may be attached to a spring such that the spacing between second drive wheel 1359 and/or the second roller wheel 1331 is adjustable for elongate shafts of medical devices having varying outer diameters.

In sum, the systems, devices, and methods discussed herein may help an operator to quickly and safely deliver medical treatment to a treatment site, for example, to break up and remove kidney stones or other hard material. As discussed above, once the device is positioned at the treatment site, there is no need to remove any portion of the device to deliver fluid, apply suction, or otherwise treat the treatment site. Furthermore, during insertion, the sheath and/or the scope may not substantially increase a cross-sectional area of the device, which may reduce the likelihood of injury to the patient.

Although the illustrative methods 1000 and 1100 are described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

As used herein, all directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure.

Although non-limiting, as used herein, the terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical device, comprising:
a scope having a proximal end, a distal end, a camera at the distal end, and a working channel extending between the proximal end and the distal end;
a sheath having a proximal end, a distal end, a distally tapered distal tip, a sheath lumen, and a wall extending between the proximal end and the distal end and defining a first lumen and a second lumen, wherein the scope extends through and is retractable within the first lumen to a position with the distal end of the scope proximal to the distal end of the sheath;
a sensor extending through the second lumen; and
a laser extending through the working channel of the scope, and extendable distally out of the distal end of the scope and into the distally tapered distal tip of the sheath lumen distal to the distal end of the scope to fragment a mass within the distally tapered distal tip of the sheath lumen and distal to the distal end of the scope;
wherein the distally tapered distal tip defines a first tip opening in fluid communication with the first lumen and a second tip opening through an outer surface of the distally tapered distal tip and through which the sensor is extendable.

2. The medical device of claim 1, wherein the laser extends through the sheath.

3. The medical device of claim 1, wherein a portion of the first lumen is defined by an exterior surface of the scope and an interior surface of the wall of the sheath.

4. The medical device of claim 1, wherein the laser extends through the second lumen.

5. The medical device of claim 1, wherein the distally tapered distal tip end of the sheath has a distally tapered internal tip wall defining a distally tapered chamber, and wherein the laser is operable to fragment a bodily mass within the distally tapered chamber.

6. The medical device of claim 1, further comprising an attachment coupled to a distal end of the sheath, wherein the attachment includes a flared section, and wherein the attachment further defines the fragmentation chamber.

* * * * *